US009630901B2

(12) United States Patent
Godlewski et al.

(10) Patent No.: US 9,630,901 B2
(45) Date of Patent: Apr. 25, 2017

(54) POLY(ACRYLIC ACID) FROM BIO-BASED ACRYLIC ACID AND ITS DERIVATIVES

(71) Applicant: The Procter & Gamble Company, Cincinnati, OH (US)

(72) Inventors: Jane Ellen Godlewski, Loveland, OH (US); Janette Villalobos, Cincinnati, OH (US); Dimitris Ioannis Collias, Mason, OH (US); Axel Meyer, Frankfurt am Main (DE); Peter Dziezok, Hochheim (DE); Juan Estaban Velasquez, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 360 days.

(21) Appl. No.: 13/760,527

(22) Filed: Feb. 6, 2013

(65) Prior Publication Data
US 2013/0274697 A1   Oct. 17, 2013

Related U.S. Application Data

(60) Provisional application No. 61/623,054, filed on Apr. 11, 2012.

(51) Int. Cl.
| | | |
|---|---|---|
| A61F 13/15 | (2006.01) |
| C07C 51/48 | (2006.01) |
| B01J 27/18 | (2006.01) |
| B01J 27/187 | (2006.01) |
| B01J 27/25 | (2006.01) |
| C07C 51/377 | (2006.01) |
| C07C 51/09 | (2006.01) |
| C07C 57/04 | (2006.01) |
| A61F 13/534 | (2006.01) |
| C08F 2/10 | (2006.01) |
| B01J 27/16 | (2006.01) |
| B01J 27/185 | (2006.01) |
| B01J 27/186 | (2006.01) |
| B01J 27/188 | (2006.01) |
| B01J 27/195 | (2006.01) |
| B01J 27/198 | (2006.01) |
| B01J 35/02 | (2006.01) |
| B01J 37/00 | (2006.01) |
| B01J 37/04 | (2006.01) |
| B01J 37/08 | (2006.01) |
| C07C 51/44 | (2006.01) |
| A61F 13/53 | (2006.01) |

(52) U.S. Cl.
CPC ............ *C07C 51/48* (2013.01); *A61F 13/534* (2013.01); *B01J 27/16* (2013.01); *B01J 27/1806* (2013.01); *B01J 27/186* (2013.01); *B01J 27/187* (2013.01); *B01J 27/188* (2013.01); *B01J 27/1811* (2013.01); *B01J 27/1817* (2013.01); *B01J 27/1853* (2013.01); *B01J 27/1856* (2013.01); *B01J 27/195* (2013.01); *B01J 27/198* (2013.01); *B01J 27/25* (2013.01); *B01J 35/023* (2013.01); *B01J 37/0036* (2013.01); *B01J 37/04* (2013.01); *B01J 37/08* (2013.01); *C07C 51/09* (2013.01); *C07C 51/377* (2013.01); *C07C 51/44* (2013.01); *C07C 57/04* (2013.01); *C08F 2/10* (2013.01); *A61F 13/53* (2013.01); *A61F 2013/530489* (2013.01); *A61F 2013/530496* (2013.01)

(58) Field of Classification Search
CPC .......... A61F 13/53; A61F 2013/530489; A61F 2013/530496
USPC ....... 604/367, 368, 374, 376, 377, 375, 372, 604/378, 385.101
See application file for complete search history.

(56) References Cited

U.S. PATENT DOCUMENTS

| | | | |
|---|---|---|---|
| 3,005,456 A * | 10/1961 | Graham, Jr ...................... 604/15 |
| 3,781,222 A | 12/1973 | Weisang et al. |
| 4,507,438 A * | 3/1985 | Obayashi et al. ............ 525/119 |
| 4,695,661 A | 9/1987 | Homann et al. |
| 2005/0209411 A1* | 9/2005 | Nestler ................... C08F 20/06 525/329.7 |
| 2006/0173432 A1* | 8/2006 | Laumer et al. ............... 604/372 |
| 2009/0275470 A1 | 11/2009 | Nagasawa et al. |
| 2009/0318885 A1* | 12/2009 | Dairoku et al. .............. 604/367 |
| 2011/0245436 A1* | 10/2011 | Gartner ..................... C08F 2/10 526/65 |
| 2011/0313113 A1 | 12/2011 | Sakamoto et al. |
| 2011/0319849 A1* | 12/2011 | Collias et al. ................ 604/372 |

FOREIGN PATENT DOCUMENTS

| | | |
|---|---|---|
| EP | 0 574 260 A1 | 12/1993 |
| EP | 2 395 029 A1 | 12/2011 |
| GB | 1489832 | 10/1977 |
| WO | WO 2005/012369 | 2/2005 |

OTHER PUBLICATIONS

Kirk-Othmer Encylcopedia of Chemical Technology, vol. 1, pp. 324-369, $5^{th}$ Ed., John Wiley & Sons, Inc., 2004.
Modern Superabsorent Polymer Technology, Buchholz and Graham eds., J. Wiley & Sons, 1998, pp. 69-117.
International Search Report and Written Opinion dated Nov. 4, 2013.

* cited by examiner

*Primary Examiner* — Jacqueline Stephens
(74) *Attorney, Agent, or Firm* — Brent M. Peebles

(57) ABSTRACT

Bio-based glacial acrylic acid, produced from hydroxypropionic acid, hydroxypropionic acid derivatives, or mixtures thereof and having impurities of hydroxypropionic acid, hydroxypropionic acid derivatives, or mixtures thereof, is polymerized to poly(acrylic acid) or superabsorbent polymer using the same processes as petroleum-derived glacial acrylic acid.

20 Claims, No Drawings

POLY(ACRYLIC ACID) FROM BIO-BASED ACRYLIC ACID AND ITS DERIVATIVES

FIELD OF THE INVENTION

The present invention generally relates to the production of poly(acrylic acid) (PAA) from bio-based acrylic acid, acrylic acid derivatives, or mixtures thereof produced from hydroxypropionic acid, hydroxypropionic acid derivatives, or mixtures thereof. More specifically, the invention relates to the polymerization of bio-based glacial acrylic acid, acrylic acid derivatives, or mixtures thereof to form PAA or superabsorbent polymer (SAP).

BACKGROUND OF THE INVENTION

Acrylic acid or acrylate has a variety of industrial uses, typically consumed in the form of polymers. In turn, these polymers are commonly used in the manufacture of, among other things, adhesives, binders, coatings, paints, polishes, detergents, flocculants, dispersants, thixotropic agents, sequestrants, and superabsorbent polymers, which are used in disposable absorbent articles including diapers and hygienic products, for example. Acrylic acid is commonly made from petroleum sources. For example, acrylic acid has long been prepared by catalytic oxidation of propylene. These and other methods of making acrylic acid from petroleum sources are described in the Kirk-Othmer Encyclopedia of Chemical Technology, Vol. 1, pgs. 342-369 ($5^{th}$ Ed., John Wiley & Sons, Inc., 2004). Petroleum-based acrylic acid contributes to greenhouse emissions due to its high petroleum derived carbon content. Furthermore, petroleum is a non-renewable material, as it takes hundreds of thousands of years to form naturally and only a short time to consume. As petrochemical resources become increasingly scarce, more expensive, and subject to regulations for $CO_2$ emissions, there exists a growing need for bio-based acrylic acid or acrylate that can serve as an alternative to petroleum-based acrylic acid or acrylate. Many attempts have been made over the last 40 to 50 years to make bio-based acrylic acid or acrylate from non-petroleum sources, such as lactic acid (also known as 2-hydroxypropionic acid), 3-hydroxypropionic acid, glycerin, carbon monoxide and ethylene oxide, carbon dioxide and ethylene, and crotonic acid.

Petroleum-based superabsorbent polymer is made by polymerization of petroleum-based acrylic acid using methods described in Buchholz and Graham (eds), *MODERN SUPERABSORENT POLYMER TECHNOLOGY*, J. Wiley & Sons, 1998, pages 69 to 117, or recent patent applications, for example U.S. Patent Applications 2009/0275470 and 2011/0313113. The petroleum-based acrylic acid used in these methods is glacial acrylic acid with purity exceeding 98% and typically being 99.5% or higher. The typical major impurities in the petroleum-based glacial acrylic acid are propionic acid, acetic acid, maleic anhydride, maleic acid, acrolein, and furfural. On the other hand, the major impurities in the bio-based glacial acrylic acid, acrylic acid derivatives, or mixtures thereof produced from hydroxypropionic acid, hydroxypropionic acid derivatives, or mixtures thereof, are propionic acid, acetic acid, and hydroxypropionic acid, hydroxypropionic acid derivatives, or mixtures thereof.

Accordingly, there is a need for commercially viable processes of polymerizing bio-based glacial acrylic acid, acrylic acid derivatives, or mixtures thereof produced from the dehydration of hydroxypropionic acid, hydroxypropionic acid derivates, or mixtures thereof, to PAA for detergents, flocculants, and other applications; and SAP for use in diapers and other applications.

SUMMARY OF THE INVENTION

In one embodiment of the present invention, a superabsorbent polymer composition is provided produced from an acrylic composition, wherein the acrylic composition comprises an acrylic acid composition, wherein the acrylic acid composition consists of acrylic acid, acrylic acid derivatives, or mixtures thereof, wherein the acrylic acid composition comprises at least about 98 wt % acrylic acid, acrylic acid derivatives, or mixtures thereof, and wherein a portion of the remaining impurities in the acrylic acid composition is hydroxypropionic acid, hydroxypropionic acid derivatives, or mixtures thereof.

In another embodiment of the present invention, a poly (acrylic acid) composition is provided produced from an acrylic composition, wherein the acrylic composition comprises an acrylic acid composition, wherein the acrylic acid composition consists of acrylic acid, acrylic acid derivatives, or mixtures thereof, wherein the acrylic acid composition comprises at least about 98 wt % acrylic acid, acrylic acid derivatives, or mixtures thereof, and wherein a portion of the remaining impurities in the acrylic acid composition is hydroxypropionic acid, hydroxypropionic acid derivatives, or mixtures thereof.

DETAILED DESCRIPTION OF THE INVENTION

I Definitions

As used herein, the term "poly(acrylic acid)" refers to homopolymers of acrylic acid, or copolymers of acrylic acid and other monomers.

As used herein, the term "superabsorbent polymer" refers to a polymer which is capable of absorbing within the polymer at least 10 times its weight in deionized water, allowing for adjustment of the pH of the system.

As used herein, the term "ion-exchange capacity" refers to the theoretical or calculated ion-exchange capacity of the polymer or polymers in milliequivalents per gram (meq/g) assuming that each un-neutralized acid or base group becomes neutralized in the ion-exchange process.

As used herein, the term "acrylic composition" refers to a composition that includes an acrylic acid composition and other materials, such as, water, other solvents, or mixtures thereof.

As used herein, the term "acrylic acid composition" refers to a composition that consists of acrylic acid, acrylic acid derivatives, or mixtures thereof.

As used herein, the term "distilled acrylic acid" refers to a composition of acrylic acid with content of acrylic acid lower than about 94 wt %.

As used herein, the term "crude acrylic acid" refers to a composition of acrylic acid with content of acrylic acid between about 94 wt % and about 98 wt %.

As used herein, the term "glacial acrylic acid" refers to a composition of acrylic acid with content of acrylic acid at least about 98 wt %.

As used herein, the term "bio-based" material refers to a renewable material.

As used herein, the term "renewable material" refers to a material that is produced from a renewable resource.

As used herein, the term "renewable resource" refers to a resource that is produced via a natural process at a rate comparable to its rate of consumption (e.g., within a 100 year time frame). The resource can be replenished naturally, or via agricultural techniques. Non-limiting examples of renewable resources include plants (e.g., sugar cane, beets, corn, potatoes, citrus fruit, woody plants, lignocellulose, hemicellulose, cellulosic waste), animals, fish, bacteria, fungi, and forestry products. These resources can be naturally occurring, hybrids, or genetically engineered organisms. Natural resources, such as crude oil, coal, natural gas, and peat, which take longer than 100 years to form, are not considered renewable resources. Because at least part of the material of the invention is derived from a renewable resource, which can sequester carbon dioxide, use of the material can reduce global warming potential and fossil fuel consumption.

As used herein, the term "bio-based content" refers to the amount of carbon from a renewable resource in a material as a percent of the weight (mass) of the total organic carbon in the material, as determined by ASTM D6866-10 Method B.

As used herein, the term "petroleum-based" material refers to a material that is produced from fossil material, such as petroleum, natural gas, coal, etc.

As used herein, the term "condensed phosphate" refers to any salts containing one or several P—O—P bonds generated by corner sharing of $PO_4$ tetrahedra.

As used herein, the term "cyclophosphate" refers to any cyclic condensed phosphate constituted of two or more corner-sharing $PO_4$ tetrahedra.

As used herein, the term "monophosphate" or "orthophosphate" refers to any salt whose anionic entity, $[PO_4]^{3-}$, is composed of four oxygen atoms arranged in an almost regular tetrahedral array about a central phosphorus atom.

As used herein, the term "oligophosphate" refers to any polyphosphates that contain five or less $PO_4$ units.

As used herein, the term "polyphosphate" refers to any condensed phosphates containing linear P—O—P linkages by corner sharing of $PO_4$ tetrahedra leading to the formation of finite chains.

As used herein, the term "ultraphosphate" refers to any condensed phosphate where at least two $PO_4$ tetrahedra of the anionic entity share three of their corners with the adjacent ones.

As used herein, the term "cation" refers to any atom or group of covalently-bonded atoms having a positive charge.

As used herein, the term "monovalent cation" refers to any cation with a positive charge of +1.

As used herein, the term "polyvalent cation" refers to any cation with a positive charge equal or greater than +2.

As used herein, the term "anion" refers to any atom or group of covalently-bonded atoms having a negative charge.

As used herein, the term "heteropolyanion" refers to any anion with covalently bonded $XO_p$ and $YO_r$ polyhedra, and thus includes X—O—Y and possibly X—O—X and Y—O—Y bonds, wherein X and Y represent any atoms, and wherein p and r are any positive integers.

As used herein, the term "heteropolyphosphate" refers to any heteropolyanion, wherein X represents phosphorus (P) and Y represents any other atom.

As used herein, the term "phosphate adduct" refers to any compound with one or more phosphate anions and one or more non-phosphate anions that are not covalently linked.

As used herein, the terms "LA" refers to lactic acid, "AA" refers to acrylic acid, "AcH" refers to acetaldehyde, and "PA" refers to propionic acid.

As used herein, the term "particle span" refers to a statistical representation of a given particle sample and is equal to $(D_{v,0.90}-D_{v,0.10})/D_{v,0.50}$. The term "median particle size" or $D_{v,0.050}$ refers to the diameter of a particle below which 50% of the total volume of particles lies. Further, $D_{v,0.10}$ refers to the particle size that separates the particle sample at the 10% by volume fraction and $D_{v,0.90}$, is the particle size that separates the particle sample at the 90% by volume fraction.

As used herein, the term "conversion" in % is defined as [hydroxypropionic acid, hydroxypropionic acid derivatives, or mixtures thereof flow rate in (mol/min)—hydroxypropionic acid, hydroxypropionic acid derivatives, or mixtures thereof flow rate out (mol/min)]/[hydroxypropionic acid, hydroxypropionic acid derivatives, or mixtures thereof flow rate in (mol/min)]*100. For the purposes of this invention, the term "conversion" means molar conversion, unless otherwise noted.

As used herein, the term "yield" in % is defined as [product flow rate out (mol/min)/hydroxypropionic acid, hydroxypropionic acid derivatives, or mixtures thereof flow rate in (mol/min)]*100. For the purposes of this invention, the term "yield" means molar yield, unless otherwise noted.

As used herein, the term "selectivity" in % is defined as [Yield/Conversion]*100. For the purposes of this invention, the term "selectivity" means molar selectivity, unless otherwise noted.

As used herein, the term "total flow rate out" in mol/min and for hydroxypropionic acid is defined as: (2/3)*[C2 flow rate out (mol/min)]+[C3 flow rate out (mol/min)]+(2/3)*[acetaldehyde flow rate out (mol/min)]+(4/3)*[C4 flow rate out (mol/min)]+[hydroxypropionic acid flow rate out (mol/min)]+[pyruvic acid flow rate out (mol/min)]+(2/3)*[acetic acid flow rate out (mol/min)]+[1,2-propanediol flow rate out (mol/min)]+[propionic acid flow rate out (mol/min)]+[acrylic acid flow rate out (mol/min)]+(5/3)*[2,3-pentanedione flow rate out (mol/min)]+(1/3)*[carbon monoxide flow rate out (mol/min)]+(1/3)*[carbon dioxide flow rate out (mol/min)]. If a hydroxypropionic acid derivative is used instead of hydroxypropionic acid, the above formula needs to be adjusted according to the number of carbon atoms in the hydroxypropionic acid derivative.

As used herein, the term "C2" means ethane and ethylene.

As used herein, the term "C3" means propane and propylene.

As used herein, the term "C4" means butane and butenes.

As used herein, the term "total molar balance" or "TMB" in % is defined as [total flow rate out (mol/min)/hydroxypropionic acid, hydroxypropionic acid derivatives, or mixtures thereof flow rate in (mol/min)]*100.

As used herein, the term "the acrylic acid yield was corrected for TMB" is defined as [acrylic acid yield/total molar balance]*100, to account for slightly higher flows in the reactor.

As used herein, the term "Gas Hourly Space Velocity" or "GHSV" in $h^{-1}$ is defined as [Total gas flow rate (mL/min)/catalyst bed volume (mL)]/60. The total gas flow rate is calculated under Standard Temperature and Pressure conditions (STP; 0° C. and 1 atm).

As used herein, the term "Liquid Hourly Space Velocity" or "LHSV" in $h^{-1}$ is defined as [Total liquid flow rate (mL/min)/catalyst bed volume (mL)]/60.

II Poly(Acrylic Acid) and its Preparation Methods

Unexpectedly it has been found that bio-based glacial acrylic acid, acrylic acid derivatives, or mixtures thereof can be polymerized to produce poly(acrylic acid) or superabsorbent polymer using processes that are similar to those used in producing poly(acrylic acid) or superabsorbent polymer from petroleum-derived glacial acrylic acid, acrylic acid derivatives, or mixtures thereof. Although the impurities that are present in bio-based acrylic acid, acrylic acid derivatives, or mixtures thereof are different than those present in the petroleum-based glacial acrylic acid, acrylic acid derivatives, or mixtures thereof, the same processes that are used to polymerize the petroleum-based glacial acrylic acid, acrylic acid derivatives, or mixtures thereof (e.g. processes for superabsorbent polymer disclosed in U.S. Pat. No. 7,307,132 (issued in 2007) and U.S. Patent Applications 2009/0275470, 2011/0306732, 2011/0313113, and 2012/0091392; all incorporated herein by reference) can be used to polymerize bio-based glacial acrylic acid, acrylic acid derivatives, or mixtures thereof.

In one embodiment, a superabsorbent polymer composition is provided and is produced from an acrylic composition, wherein the acrylic composition comprises an acrylic acid composition, wherein the acrylic acid composition consists of acrylic acid, acrylic acid derivatives, or mixtures thereof, wherein the acrylic acid composition comprises at least about 98 wt % acrylic acid, acrylic acid derivatives, or mixtures thereof, and wherein a portion of the remaining impurities in the acrylic acid composition is hydroxypropionic acid, hydroxypropionic acid derivatives, or mixtures thereof.

The acrylic composition comprises the acrylic acid composition and optionally other materials, such as, by way of example and not limitation, water, other solvents, or mixtures thereof.

Hydroxypropionic acid can be 3-hydroxypropionic acid, 2-hydroxypropionic acid (also called, lactic acid), 2-methyl hydroxypropionic acid, or mixtures thereof. Derivatives of hydroxypropionic acid can be metal or ammonium salts of hydroxypropionic acid, alkyl esters of hydroxypropionic acid, alkyl esters of 2-methyl hydroxypropionic acid, cyclic di-esters of hydroxypropionic acid, hydroxypropionic acid anhydride, or a mixture thereof. Non-limiting examples of metal salts of hydroxypropionic acid are sodium hydroxypropionate, potassium hydroxypropionate, and calcium hydroxypropionate. Non-limiting examples of alkyl esters of hydroxypropionic acid are methyl hydroxypropionate, ethyl hydroxypropionate, butyl hydroxypropionate, 2-ethylhexyl hydroxypropionate, or mixtures thereof. A non-limiting example of cyclic di-esters of hydroxypropionic acid is dilactide.

In one embodiment, the hydroxypropionic acid is lactic acid or 2-methyl lactic acid. In another embodiment, the hydroxypropionic acid is lactic acid. Lactic acid can be L-lactic acid, D-lactic acid, or mixtures thereof. In one embodiment, the hydroxypropionic acid, hydroxypropionic acid derivatives, or mixtures thereof in the impurities in the glacial acrylic acid composition are lactic acid, lactic acid derivatives, or mixtures thereof.

The acrylic acid derivatives can be acrylic acid oligomers, metal or ammonium salts of monomeric acrylic acid, metal or ammonium salts of acrylic acid oligomers, or mixtures thereof. Non-limiting examples of metal salts of acrylic acid are sodium acrylate and potassium acrylate. Non-limiting examples of alkyl esters of acrylic acid are methyl lactate, ethyl lactate, or mixtures thereof.

The acrylic acid, acrylic acid derivatives, or mixtures thereof can be made from renewable resources or materials. Non-limiting examples of renewable resources or materials are hydroxypropionic acid, hydroxypropionic acid derivatives, or mixtures thereof; glycerin; carbon monoxide and ethylene oxide; carbon dioxide and ethylene; and crotonic acid. In one embodiment, the renewable resources or materials are hydroxypropionic acid, hydroxypropionic acid derivatives, or mixtures thereof. In another embodiment, the renewable resources or materials are lactic acid, lactic acid derivatives, or mixtures thereof. In yet another embodiment, the renewable resource or material is lactic acid.

In one embodiment, the superabsorbent polymer composition is produced by the steps comprising: a) preparing a pre-polymerization solution containing: (i) the acrylic composition, and (ii) a solvent; and wherein, the pH of the pre-polymerization solution is less than about 6; b) combining an initiator with the pre-polymerization solution to produce a polymerization mixture; c) polymerizing the polymerization mixture to produce a gel; and d) drying the gel to produce the superabsorbent polymer composition.

In another embodiment, the superabsorbent polymer composition is produced by the steps comprising: a) preparing a pre-polymerization solution comprising: (i) the acrylic composition, and (ii) a solvent; b) mixing a base into the pre-polymerization solution to form a partially neutralized acrylic acid solution, and wherein, the pH of the partially neutralized acrylic acid solution is less than about 6; c) combining an initiator with the partially neutralized acrylic acid solution to produce a polymerization mixture; d) polymerizing the polymerization mixture to produce a gel; and e) drying the gel to produce the superabsorbent polymer composition.

In one embodiment, the superabsorbent polymer composition is produced by the steps comprising: a) preparing a pre-polymerization solution containing: (i) the acrylic composition, and (ii) a solvent; and wherein, the pH of the pre-polymerization solution is less than about 6; b) combining an initiator with the pre-polymerization solution to produce a polymerization mixture; c) polymerizing the polymerization mixture to produce a gel; d) adding a crosslinking agent to the gel to produce a crosslinked surface polymer; and e) drying the crosslinked surface polymer to produce the superabsorbent polymer composition.

In another embodiment, the superabsorbent polymer composition is produced by the steps comprising: a) preparing a pre-polymerization solution comprising: (i) the acrylic composition, and (ii) a solvent; b) mixing a base into the pre-polymerization solution to form a partially neutralized acrylic acid solution, and wherein, the pH of the partially neutralized acrylic acid solution is less than about 6; c) combining an initiator with the partially neutralized acrylic acid solution to produce a polymerization mixture; d) polymerizing the polymerization mixture to produce a gel; e) adding a crosslinking agent to the gel to produce a crosslinked surface polymer; and f) drying the crosslinked surface polymer to produce the superabsorbent polymer composition.

In another embodiment, the superabsorbent polymer composition is produced by the steps comprising: a) preparing a pre-polymerization solution comprising: glacial acrylic acid, methylene bis-acrylamide, and water; b) mixing sodium hydroxide into the pre-polymerization solution to form a partially neutralized acrylic acid solution; c) combining 2,2'-azobis(2-methylpropionamidine)dihydrochloride with the partially neutralized acrylic acid solution to produce a polymerization mixture; d) polymerizing the polymerization mixture using UV light to produce a gel; and e) drying the gel to produce the superabsorbent polymer composition.

In one embodiment, the solvent of the pre-polymerization solution is selected from the group comprising water, organic solvents, and mixtures thereof. In yet another embodiment, the solvent of the pre-polymerization solution is water. In another embodiment, the pH of the pre-polymerization solution is between about 3 and about 5. In another embodiment, the pH of the partially neutralized acrylic acid solution is between about 3 and about 5.

In another embodiment, the amount of the acrylic acid composition in the pre-polymerization solution is from about 5 wt % to about 95 wt %. In another embodiment, the amount of water in the pre-polymerization solution is from about 5 wt % to about 95 wt %. In yet another embodiment, the pre-polymerization solution further comprises a dispersing aid. In one embodiment, the dispersing aid is carboxymethyl cellulose (CMC).

In another embodiment, the pre-polymerization solution further comprises a crosslinking agent. In yet another embodiment, the crosslinking agent is present in an amount of less than about 10 wt %, based on the total amount of said acrylic acid composition in said pre-polymerization solution. In one embodiment, the crosslinking agent is selected from the group consisting of di- or poly-functional monomers, having two or more groups that can be polymerized, such as N,N'-methylenebisacrylamide, trimethylolpropane triacrylate, ethylene glycol di(meth)acrylate, or triallylamine, and other organic crosslinking agents that may be apparent to those having ordinary skills in the art.

In one embodiment, the initiator is an amount from about 0.01% wt % to about 10 wt %, based on the total amount of the acrylic acid composition in the pre-polymerization solution. In another embodiment, the initiator can be added as a solid or in combination with an initiator solvent, wherein the initiator and initiator solvent are forming a liquid solution or dispersion. A non-limiting example of the initiator solvent is water. Non-limiting examples of initiators are chemical compounds selected from the group comprising hydroperoxides, hydrogen peroxide, organic peroxides, azo compounds, persulfates, other redox initiators, and mixtures thereof. Non-limiting examples of hydroperoxides are tert-butyl hydroperoxide and cumene hydroperoxide. Non-limiting examples of organic peroxides are acetylacetone peroxide, methyl ethyl ketone peroxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl) peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-tri-methylhexanoate, acetylcyclohexylsulfonyl peroxide, dilauryl peroxide, dibenzoyl peroxide, and tert-amyl perneodecanoate. Non-limiting examples of azo compounds are 2,2'-azobisisobutyronitrile, 2,2'-azobis(2,4-dimethylvaleronitrile), 2,2'-azobis(4-methoxy-2,4-dimethyl-valeronitrile), 2,2'-azobis-{2-[1-(2-hydroxyethyl)-2-imidazolin-2-yl]propane}dihydrochloride, 2,2'-azobis-(2-amidinopropane) dihydrochloride, 2,2'-azobis[2-(2-imidazolin-2-yl)propane]dihydrochloride, and 2,2'-azobis[2-(5-methyl-2-imidazolin-2-yl)propane]dihydrochloride. Non-limiting examples of persulfates are sodium peroxodisulfate, potassium peroxodisulfate and ammonium peroxodisulfate. In another embodiment, a mixture of two or more initiators is used.

In another embodiment, a polymerization catalyst can be used. A non-limiting example of a polymerization catalyst is TMEDA (N,N,N',N'-tetramethylethylenediamine). Polymerization methods to prepare the superabsorbent polymer composition can include free radical, ring-opening, condensation, anionic, cationic, or irradiation techniques. The polymerization rate can be controlled through the identity and amount of initiators and the polymerization temperature.

The polymerization of the acrylic acid composition can be highly exothermic, and hence, in one embodiment, the polymerization solution can be cooled during polymerization.

In one embodiment, the partially neutralized acrylic acid solution comprises at least about 20 mol % of an acrylic acid salt, based on the total amount of the acrylic acid composition, and wherein the acrylic acid salt is produced in the mixing step. In another embodiment, the partially neutralized acrylic acid solution comprises at least about 40 mol % of an acrylic acid salt, based on the total amount of the acrylic acid composition, and wherein the acrylic acid salt is produced in the mixing step. In another embodiment, the partially neutralized acrylic acid solution comprises at least about 60 mol % of an acrylic acid salt, based on the total amount of the acrylic acid composition, and wherein the acrylic acid salt is produced in the mixing step. In another embodiment, the partially neutralized acrylic acid solution comprises at least about 80 mol % of an acrylic acid salt, based on the total amount of the acrylic acid composition, and wherein the acrylic acid salt is produced in the mixing step.

In one embodiment, at least about 20 mol % of the acrylic acid composition in the partially neutralized acrylic acid solution contains a carboxylate group with a cationic counter ion. In another embodiment, at least about 40 mol % of the acrylic acid composition in the partially neutralized acrylic acid solution contains a carboxylate group with a cationic counter ion. In another embodiment, at least about 60 mol % of the acrylic acid composition in the partially neutralized acrylic acid solution contains a carboxylate group with a cationic counter ion. In another embodiment, at least about 80 mol % of the acrylic acid composition in the partially neutralized acrylic acid solution contains a carboxylate group with a cationic counter ion. Non-limiting examples of bases are sodium hydroxide and potassium hydroxide.

In another embodiment, a crosslinking agent is added to the gel after the polymerization is completed to produce a crosslinked surface polymer, and the crosslinked surface polymer is dried to produce the superabsorbent polymer composition. Surface crosslinking of the initially formed polymers is a preferred process for obtaining superabsorbent polymers having relatively high performance under pressure (PUP) capacity, porosity and permeability. Non-limiting examples of processes to produce a crosslinked surface polymer are: those where a) a di- or poly-functional reagent (s) capable of reacting with existing functional groups within the superabsorbent polymer is applied to the surface of the polymer; b) a di- or poly-functional reagent that is capable of reacting with other added reagents and possibly existing functional groups within the absorbent polymer such as to increase the level of crosslinking at the surface is applied to the surface; c) additional reaction (s) is induced amongst existing components within the superabsorbent polymer, such as to generate a higher level of crosslinking at or near the surface; among others that may be apparent to those having skill in the art.

In one embodiment, the superabsorbent polymer composition comprises: a) a cation-exchange absorbent polymer prepared from an acrylic composition, wherein the acrylic composition comprises an acrylic acid composition, wherein the acrylic acid composition consists of acrylic acid, acrylic acid derivatives, or mixtures thereof, wherein the acrylic acid composition comprises at least about 98 wt % acrylic acid, acrylic acid derivatives, or mixtures thereof, and wherein a portion of the remaining impurities in the acrylic acid composition is hydroxypropionic acid, hydroxypropionic acid derivatives, or mixtures thereof; and b) an anion-exchange absorbent polymer, wherein the ion-exchange capacity of the anion-exchange absorbent polymer is at least about 15 meq/g.

In one embodiment, the hydroxypropionic acid, hydroxypropionic acid derivatives, or mixtures thereof in the impurities in the glacial acrylic acid composition are lactic acid, lactic acid derivatives, or mixtures thereof.

In another embodiment, the cation-exchange absorbent polymer is from about 80% to about 100% in the un-neutralized acid form and the anion-exchange absorbent polymer is from about 80% to about 100% in the un-neutralized base form. In another embodiment, the anion-exchange absorbent polymer is prepared from a monomer selected from the group consisting of ethylenimine, allylamine, diallylamine, 4-aminobutene, alkyl oxazolines, vinylformamide, 5-aminopentene, carbodiimides, formaldazine, and melamine; a secondary amine derivative of any of the foregoing; a tertiary amine derivative of any of the foregoing; and mixtures therefore. In another embodiment, the anion-exchange absorbent polymer is prepared from a monomer selected from the group consisting of ethylenimine, allylamine, diallylamine, and mixtures thereof.

In another embodiment, the superabsorbent polymer composition comprises: a) the anion-exchange absorbent polymer selected from the group consisting of poly(ethylenimine); poly(allylamine); and mixtures thereof; and b) the cation-exchange polymer is a homopolymer or copolymer of the acrylic acid prepared from an acrylic composition, wherein the acrylic composition comprises an acrylic acid composition, wherein the acrylic acid composition consists of acrylic acid, acrylic acid derivatives, or mixtures thereof, wherein the acrylic acid composition comprises at least about 98 wt % acrylic acid, acrylic acid derivatives, or mixtures thereof, and wherein a portion of the remaining impurities in the acrylic acid composition is hydroxypropionic acid, hydroxypropionic acid derivatives, or mixtures thereof. In another embodiment, the cation-exchange absorbent polymer is homogenously crosslinked.

In one embodiment, the bio-based content of the acrylic acid composition is greater than about 3%. In another embodiment, the bio-based content of the acrylic acid composition is greater than 30%. In yet another embodiment, the bio-based content of the acrylic acid composition is greater than about 90%. In one embodiment, the bio-based content of the superabsorbent polymer composition is greater than about 3%. In another embodiment, the bio-based content of the superabsorbent polymer composition is greater than 30%. In yet another embodiment, the bio-based content of the superabsorbent polymer composition is greater than about 90%.

In one embodiment, the superabsorbent polymer composition has a cylinder retention capacity (CRC) between about 20 g/g and about 45 g/g. In another embodiment, the superabsorbent polymer composition has a cylinder retention capacity (CRC) between about 25 g/g and about 40 g/g. In yet another embodiment, the superabsorbent polymer composition has a cylinder retention capacity (CRC) between about 30 g/g and about 35 g/g.

In one embodiment, the superabsorbent polymer composition has an extractables value from about 0 wt % to about 20 wt %. In another embodiment, the superabsorbent polymer composition has an extractables value from about 3 wt % to about 15 wt %. In yet another embodiment, the superabsorbent polymer composition has an extractables value from about 5 wt % to about 10 wt %.

In one embodiment, the superabsorbent polymer composition has absorption against pressure (AAP) between about 15 g/g and about 40 g/g. In another embodiment, the superabsorbent polymer composition has absorption against pressure (AAP) between about 20 g/g and about 35 g/g. In yet another embodiment, the superabsorbent polymer composition has absorption against pressure (AAP) between about 25 g/g and about 30 g/g.

In one embodiment, the amount of residual monomers in the superabsorbent polymer composition is about 500 ppm or less.

In one embodiment, an absorbent article is provided and is selected from adult incontinence garments, infant diapers, and feminine hygiene articles, and produced from an acrylic composition, wherein the acrylic composition comprises an acrylic acid composition, wherein the acrylic acid composition consists of acrylic acid, acrylic acid derivatives, or mixtures thereof, wherein the acrylic acid composition comprises at least about 98 wt % acrylic acid, acrylic acid derivatives, or mixtures thereof, and wherein a portion of the remaining impurities in the acrylic acid composition is hydroxypropionic acid, hydroxypropionic acid derivatives, or mixtures thereof.

In another embodiment, an absorbent article is provided having opposing longitudinal edges and comprising: a) a top sheet; b) a back sheet joined with the top sheet; and c) an absorbent core disposed between the top sheet and the back sheet, and wherein, the absorbent core comprises a superabsorbent polymer composition produced from an acrylic composition, wherein the acrylic composition comprises an acrylic acid composition, wherein the acrylic acid composition consists of acrylic acid, acrylic acid derivatives, or mixtures thereof, wherein the acrylic acid composition comprises at least about 98 wt % acrylic acid, acrylic acid derivatives, or mixtures thereof, and wherein a portion of the remaining impurities in the acrylic acid composition is hydroxypropionic acid, hydroxypropionic acid derivatives, or mixtures thereof.

In one embodiment, an absorbent member comprises an agglomerate of: a) particulate superabsorbent polymer composition prepared from an acrylic composition, wherein the acrylic composition comprises an acrylic acid composition, wherein the acrylic acid composition consists of acrylic acid, acrylic acid derivatives, or mixtures thereof, wherein the acrylic acid composition comprises at least about 98 wt % acrylic acid, acrylic acid derivatives, or mixtures thereof, and wherein a portion of the remaining impurities in the acrylic acid composition is hydroxypropionic acid, hydroxypropionic acid derivatives, or mixtures thereof; and b) particulate high surface area open-celled hydrophilic foam, wherein the foam, in combination with the superabsorbent polymer composition, provides the absorbent member with high capillary sorption absorbent capacity. The absorbent member is useful in the containment (e.g. storage) of body liquid fluids such as urine. As used herein, the term "agglomerate" refers to a unitary combination of particulate materials that is not easily separable, i.e. the agglomerate does not substantially separate into its component particles as a result of normal manufacturing, normal shipping, and/or normal use. High surface area foams useful herein are those that are relatively open-celled, i.e. many of the individual cells of the foam are in unobstructed communication with adjoining cells, allowing liquid transfer from one cell to the other within the foam structure. In addition to being open-celled, these high surface area foams are sufficiently hydrophilic to permit the foam to absorb aqueous liquids.

In another embodiment, the high surface area open-celled hydrophilic foam is obtained by polymerizing a high internal phase water-in-oil emulsion (HIPE). In another embodiment, a hydratable, and preferably hygroscopic or deliquescent, water soluble inorganic salt is incorporated into the HIPE. Non-limiting examples of water soluble inorganic salts are alkaline earth metal salts, such as calcium chloride. In one embodiment, the agglomerate comprises from about 1 wt % to about 98 wt % high surface area open-celled hydrophilic foam, based on the total weight of the agglomerate. In another embodiment, the agglomerate comprises from about 15 wt % to about 85 wt % high surface area open-celled hydrophilic foam, based on the total weight of the agglomerate. In yet another embodiment, the agglomerate comprises from about 30 wt % to about 40 wt % high surface area open-celled hydrophilic foam, based on the total weight of the agglomerate.

In another embodiment, a poly(acrylic acid) composition is provided and is produced from an acrylic composition, wherein the acrylic composition comprises an acrylic acid composition, wherein the acrylic acid composition consists of acrylic acid, acrylic acid derivatives, or mixtures thereof, wherein the acrylic acid composition comprises at least about 98 wt % acrylic acid, acrylic acid derivatives, or mixtures thereof, and wherein a portion of the remaining impurities in the acrylic acid composition is hydroxypropionic acid, hydroxypropionic acid derivatives, or mixtures thereof.

III Catalysts for the Conversion of Hydroxypropionic Acid or its Derivatives to Acrylic Acid or its Derivatives In one embodiment, the acrylic acid composition is produced from hydroxypropionic acid, hydroxypropionic acid derivatives, and mixtures thereof by using a catalyst. In another embodiment, the catalyst comprises: (a) at least one condensed phosphate anion selected from the group consisting of formulae (I), (II), and (III), $$[P_nO_{3n+1}]^{(n+2)-} \quad \text{(I)}$$

$$[P_nO_{3n}]^{n-} \quad \text{(II)}$$

$$[P_{(2m+n)}O_{(5m+3n)}]^{n-} \quad \text{(III)}$$

wherein n is at least 2 and m is at least 1, and (b) at least two different cations, wherein the catalyst is essentially neutrally charged, and further, wherein the molar ratio of phosphorus to the at least two different cations is between about 0.7 and about 1.7.

The anions defined by formulae (I), (II), and (III) are also referred to as polyphosphates (or oligophosphates), cyclophosphates, and ultraphosphates, respectively.

In another embodiment, the catalyst comprises: (a) at least one condensed phosphate anion selected from the group consisting of formulae (I) and (II), $$[P_nO_{3n+1}]^{(n+2)-} \quad \text{(I)}$$

$$[P_nO_{3n}]^{n-} \quad \text{(II)}$$

wherein n is at least 2, and (b) at least two different cations, wherein the catalyst is essentially neutrally charged, and further, wherein the molar ratio of phosphorus to the at least two different cations is between about 0.7 and about 1.7.

The cations can be monovalent or polyvalent. In one embodiment, one cation is monovalent and the other cation is polyvalent. In another embodiment, the polyvalent cation is selected from the group consisting of divalent cations, trivalent cations, tetravalent cations, pentavalent cations, and mixtures thereof. Non-limiting examples of monovalent cations are $H^+$, $Li^+$, $Na^+$, $K^+$, $Rb^+$, $Cs^+$, $Ag^+$, $Rb^+$, $Tl^+$, and mixtures thereof. In one embodiment, the monovalent cation is selected from the group consisting of $Li^+$, $Na^+$, $K^+$, $Rb^+$, $Cs^+$, and mixtures thereof; in another embodiment, the monovalent cation is $Na^+$ or $K^+$; and in yet another embodiment, the monovalent cation is $K^+$. Non-limiting examples of polyvalent cations are cations of the alkaline earth metals (i.e., Be, Mg, Ca, Sr, Ba, and Ra), transition metals (e.g. Y, Ti, Zr, V, Nb, Cr, Mo, Mn, Re, Fe, Ru, Co, Rh, Ni, Pd, Pt, Cu, Ag, and Au), poor metals (e.g. Zn, Ga, Si, Ge, B, Al, In, Sb, Sn, Bi, and Pb), lanthanides (e.g. La and Ce), and actinides (e.g. Ac and Th). In one embodiment, the polyvalent cation is selected from the group consisting of $Be^{2+}$, $Mg^{2+}$, $Ca^{2+}$, $Sr^{2+}$, $Ba^{2+}$, $Mn^{2+}$, $Fe^{2+}$, $Co^{2+}$, $Ni^{2+}$, $Cu^{2+}$, $Zn^{2+}$, $Cd^{2+}$, $Sn^{2+}$, $Pb^{2+}$, $Ti^{3+}$, $Cr^{3+}$, $Mn^{3+}$, $Fe^{3+}$, $Al^{3+}$, $Ga^{3+}$, $Y^{3+}$, $In^{3+}$, $Sb^{3+}$, $Bi^{3+}$, $Si^{4+}$, $Ti^{4+}$, $V^{4+}$, $Ge^{4+}$, $Mo^{4+}$, $Pt^{4+}$, $V^{5+}$, $Nb^{5+}$, $Sb^{5+}$, and mixtures thereof. In one embodiment, the polyvalent cation is selected from the group consisting of $Ca^{2+}$, $Ba^{2+}$, $Cu^{2+}$, $Mn^{2+}$, $Mn^{3+}$, and mixtures thereof; in another embodiment, the polyvalent cation is selected from the group consisting of $Ca^{2+}$, $Ba^{2+}$, $Mn^{3+}$, and mixtures thereof; and in yet another embodiment, the polyvalent cation is $Ba^{2+}$.

The catalyst can include cations: (a) $H^+$, $Li^+$, $Na^+$, $K^+$, $Rb^+$, $Cs^+$, or mixtures thereof; and (b) $Be^{2+}$, $Mg^{2+}$, $Ca^{2+}$, $Sr^{2+}$, $Ba^{2+}$, $Mn^{2+}$, $Fe^{2+}$, $Co^{2+}$, $Ni^{2+}$, $Cu^{2+}$, $Zn^{2+}$, $Cd^{2+}$, $Sn_{2+}$, $Pb^{2+}$, $Ti^{3+}$, $Cr^{3+}$, $Mn^{3+}$, $Fe^{3+}$, $Al^{3+}$, $Ga^{3+}$, $Y^{3+}$, $In^{3+}$, $Sb^{3+}$, $Bi^{3+}$, $Si^{4+}$, $Ti^{4+}$, $V^{4+}$, $Ge^{4+}$, $Mo^{4+}$, $Pt^{4+}$, $V^{5+}$, $Nb^{5+}$, $Sb^{5+}$, or mixtures thereof. In one embodiment the catalyst comprises $Li^+$, $Na^+$, or $K^+$ as monovalent cation, and $Ca^{2+}$, $Ba^{2+}$, or $Mn^{3+}$ as polyvalent cation; in another embodiment, the catalyst comprises $Na^+$ or $K^+$ as monovalent cation, and $Ca^{2+}$ or $Ba^{2+}$ as polyvalent cation; and in yet another embodiment, the catalyst comprises $K^+$ as the monovalent cation and $Ba^{2+}$ as the polyvalent cation.

In one embodiment, the catalyst comprises $Ba_{2-x-s}K_{2x}H_{2s}P_2O_7$ and $(KPO_3)_n$, wherein x and s are greater or equal to 0 and less than about 0.5 and n is a positive integer. In another embodiment, the catalyst comprises $Ca_{2-x-s}K_{2x}H_{2s}P_2O_7$ and $(KPO_3)_n$, wherein x and s are greater or equal to 0 and less than about 0.5 and n is a positive integer. In yet another embodiment, the catalyst comprises $Mn_{1-x-s}K_{1+3x}H_{3s}P_2O_7$ or $Mn_{1-x-s}K_{2+2x}H_{2s}P_2O_7$ and $(KPO_3)_n$ wherein x and s are greater or equal to 0 and less than about 0.5 and n is a positive integer. In another embodiment, the catalyst comprises any blend of $Ba_{2-x-s}K_{2x}H_{2s}P_2O_7$, $Ca_{2-x-s}K_{2x}P_2O_7$, $Mn_{1-x-s}K_{1+3x}H_{3s}P_2O_7$ or $Mn_{1-x-s}K_{2+2x}H_{2s}P_2O_7$; and $(KPO_3)_n$, wherein x and s are greater or equal to 0 and less than about 0.5 and n is a positive integer.

In one embodiment, the molar ratio of phosphorus to the cations in the catalyst is between about 0.7 and about 1.7; in another embodiment, the molar ratio of phosphorus to the cations in the catalyst is between about 0.8 and about 1.3; and in yet another embodiment, the molar ratio of phosphorus to the cations in the catalyst is about 1.

In one embodiment, the catalyst comprises: (a) at least two different condensed phosphate anions selected from the group consisting of formulae (I), (II), and (III), $$[P_nO_{3n+1}]^{(n+2)-} \quad \text{(I)}$$

$$[P_nO_{3n}]^{n-} \quad \text{(II)}$$

$$[P_{(2m+n)}O_{(5m+3n)}]^{n-} \quad \text{(III)}$$

wherein n is at least 2 and m is at least 1, and (b) one cation, wherein the catalyst is essentially neutrally charged, and further, wherein the molar ratio of phosphorus to the cation is between about 0.5 and about 4.0. In another embodiment, the molar ratio of phosphorus to the cation is between about t/2 and about t, wherein t is the charge of the cation.

The catalyst can include an inert support that is constructed of a material comprising silicates, aluminates, carbons, metal oxides, and mixtures thereof. Alternatively, the carrier is inert relative to the reaction mixture expected to contact the catalyst. In the context of the reactions expressly described herein, in one embodiment the carrier is a low surface area silica or zirconia. When present, the carrier represents an amount of about 5 wt % to about 98 wt %, based on the total weight of the catalyst. Generally, a catalyst that includes an inert support can be made by one of two exemplary methods: impregnation or co-precipitation. In the impregnation method, a suspension of the solid inert support is treated with a solution of a pre-catalyst, and the resulting material is then activated under conditions that will convert the pre-catalyst to a more active state. In the co-precipitation method, a homogenous solution of the catalyst ingredients is precipitated by the addition of additional ingredients.

In another embodiment, the catalyst can be sulfate salts; phosphate salts; mixtures of sulfate and phosphate salts; bases; zeolites or modified zeolites; metal oxides or modified metal oxides; supercritical water, or mixtures thereof.

IV Catalyst Preparation Methods

In one embodiment, the method of preparing the catalyst includes mixing and heating at least two different phosphorus containing compounds, wherein each the compound is described by one of the formulae (IV) to (XXV), or any of the hydrated forms of the formulae:

$$M^I_y(H_{3-y}PO_4) \quad (IV)$$

$$M^{II}_y(H_{3-y}PO_4)_2 \quad (V)$$

$$M^{III}_y(H_{3-y}PO_4)_3 \quad (VI)$$

$$M^{IV}_y(H_{3-y}PO_4)_4 \quad (VII)$$

$$(NH_4)_y(H_{3-y}PO_4) \quad (VIII)$$

$$M^{II}_a(OH)_b(PO_4)_c \quad (IX)$$

$$M^{III}_d(OH)_e(PO_4)_f \quad (X)$$

$$M^{II}M^I PO_4 \quad (XI)$$

$$M^{III}M^I_3(PO_4)_2 \quad (XII)$$

$$M^{IV}_2M^I PO_4)_2 \quad (XIII)$$

$$M^I_z H_{4-z}P_2O_7 \quad (XIV)$$

$$M^{II}_v H_{(4-2v)}P_2O_7 \quad (XV)$$

$$M^{IV}P_2O_7 \quad ((XVI)$$

$$(NH_4)_z H_{4-z}P_2O_7 \quad (XVII)$$

$$M^{III}M^I P_2O_7 \quad (XVIII)$$

$$M^I H_w(PO_3)_{(1+w)} \quad (XIX)$$

$$M^{II}H_w(PO_3)_{(2+w)} \quad (XX)$$

$$M^{III}H_w(PO_3)_{(3+w)} \quad (XXI)$$

$$M^{IV}H_w(PO_3)_{(4+w)} \quad (XXII)$$

$$M^{II}_g M^I_h(PO_3)_i \quad (XXIII)$$

$$M^{III}_j M^I_k(PO_3)_l \quad (XXIV)$$

$$P_2O_5 \quad (XXV)$$

wherein $M^I$ is a monovalent cation; wherein $M^{II}$ is a divalent cation; wherein $M^{III}$ is a trivalent cation; wherein $M^{IV}$ is a tetravalent cation; wherein y is 0, 1, 2, or 3; wherein z is 0, 1, 2, 3, or 4; wherein v is 0, 1, or 2; wherein w is 0 or any positive integer; and wherein a, b, c, d, e, f, g, h, i, j, k, and l are any positive integers, such that the equations: 2a=b+3c, 3d=e+3f, i=2g+h, and l=3j+k are satisfied.

In one embodiment, the catalyst is prepared by mixing and heating one or more phosphorus containing compounds of formula (IV), wherein y is equal to 1, and one or more phosphorus containing compounds of formula (V), wherein y is equal to 2. In another embodiment, the catalyst is prepared by mixing and heating $M^I H_2PO_4$ and $M^{II}HPO_4$. In one embodiment, $M^I$ is $K^+$ and $M^{II}$ is $Ca^{2+}$, i.e., the catalyst is prepared by mixing and heating $KH_2PO_4$ and $CaHPO_4$; or $M^I$ is K and $M^{II}$ is $Ba^{2+}$, i.e., the catalyst is prepared by mixing and heating $KH_2PO_4$ and $BaHPO_4$.

In one embodiment, the catalyst is prepared by mixing and heating one or more phosphorus containing compound of formula (IV), wherein y is equal to 1, one or more phosphorus containing compounds of formula (XV), wherein v is equal to 2. In another embodiment, the catalyst is prepared by mixing and heating $M^I H_2PO_4$ and $M^{II}_2P_2O_7$. In one embodiment, $M^I$ is $K^+$ and $M^{II}$ is $Ca^{2+}$, i.e., the catalyst is prepared by mixing and heating $KH_2PO_4$ and $Ca_2P_2O_7$; or $M^I$ is $K^+$ and $M^{II}$ is $Ba^{2+}$, i.e., the catalyst is prepared by mixing and heating $KH_2PO_4$ and $Ba_2P_2O_7$.

In another embodiment, the molar ratio of phosphorus to the cations in the catalyst is between about 0.7 and about 1.7; in yet another embodiment, the molar ratio of phosphorus to the cations in the catalyst is between about 0.8 and about 1.3; and in another embodiment, the molar ratio of phosphorus to the cations in the catalyst is about 1.

In another embodiment, the method of preparing the catalyst includes mixing and heating (a) at least one phosphorus containing compound, wherein each the compound is described by one of the formulae (IV) to (XXV), or any of the hydrated forms of the formulae:

$$M^I_y(H_{3-y}PO_4) \quad (IV)$$

$$M^{II}_y(H_{3-y}PO_4)_2 \quad (V)$$

$$M^{III}_y(H_{3-y}PO_4)_3 \quad (VI)$$

$$M^{IV}_y(H_{3-y}PO_4)_4 \quad (VII)$$

$$(NH_4)_y(H_{3-y}PO_4) \quad (VIII)$$

$$M^{II}_a(OH)_b(PO_4)_c \quad (IX)$$

$$M^{III}_d(OH)_e(PO_4)_f \quad (X)$$

$$M^{II}M^I PO_4 \quad (XI)$$

$$M^{III}M^I_3(PO_4)_2 \quad (XII)$$

$$M^{IV}_2M^I PO_4)_3 \quad (XIII)$$

$$M^I_z H_{4-z}P_2O_7 \quad (XIV)$$

$$M^{II}_v H_{(4-2v)}P_2O_7 \quad (XV)$$

$$M^{IV}P_2O_7 \quad ((XVI)$$

$(NH_4)_zH_{4-z}P_2O_7$ (XVII)

$M^{III}M^IP_2O_7$ (XVIII)

$M^IH_w(PO_3)_{(1+w)}$ (XIX)

$M^{II}H_w(PO_3)_{(2+w)}$ (XX)

$M^{III}H_w(PO_3)_{(3+w)}$ (XXI)

$M^{IV}H_w(PO_3)_{(4+w)}$ (XXII)

$M^{II}_gM^I_h(PO_3)_i$ (XXIII)

$M^{III}_jM^I_k(PO_3)_l$ (XXIV)

$P_2O_5$ (XXV)

wherein y is 0, 1, 2, or 3; wherein z is 0, 1, 2, 3, or 4; wherein v is 0, 1, or 2; wherein w is 0 or any positive integer; and wherein a, b, c, d, e, f, g, h, i, j, k, and l are any positive integers, such that the equations: 2a=b+3c, 3d=e+3f, i=2g+h, and l=3j+k are satisfied, and (b) at least one non-phosphorus containing compound selected from the group consisting of nitrate salts, carbonate salts, acetate salts, metal oxides, chloride salts, sulfate salts, and metal hydroxides, wherein each the compound is described by one of the formulae (XXVI) to (XL), or any of the hydrated forms of the formulae:

$M^INO_3$ (XXVI)

$M^{II}(NO_3)_2$ (XXVII)

$M^{III}(NO_3)_3$ (XXVIII)

$M^I_2CO_3$ (XXIX)

$M^{II}_2CO_3$ (XXX)

$M^{III}_2(CO_3)_3$ (XXXI)

$(CH_3COO)M^I$ (XXXII)

$(CH_3COO)_2M^{II}$ (XXXIII)

$(CH_3COO)_3M^{III}$ (XXXIV)

$(CH_3COO)_4M^{IV}$ (XXXV)

$M^I_2O$ (XXXVI)

$M^{II}O$ (XXXVII)

$M^{III}_2O_2$ (XXXVIII)

$M^{IV}O_2$ (XXXIX)

$M^ICl$ (XXXX)

$M^{II}Cl_2$ (XXXXI)

$M^{III}Cl_3$ (XXXXII)

$M^{IV}Cl_4$ (XXXXIII)

$M^I_2SO_4$ (XXXXIV)

$M^{II}SO_4$ (XXXXV)

$M^{III}_2(SO_4)_3$ (XXXXVI)

$M^{IV}(SO_4)_2$ (XXXXVII)

$M^IOH$ (XXXVIII)

$M^{II}(OH)_2$ (XXXIX)

$M^{III}(OH)_3$ (XL).

In another embodiment, the non-phosphorus containing compounds can be selected from the group consisting of carboxylic acid-derived salts, halide salts, metal acetylacetonates, and metal alkoxides.

In one embodiment of the present invention, the molar ratio of phosphorus to the cations in the catalyst is between about 0.7 and about 1.7; in another embodiment, the molar ratio of phosphorus to the cations in the catalyst is between about 0.8 and about 1.3; and in yet another embodiment, the molar ratio of phosphorus to the cations in the catalyst is about 1.

In another embodiment of the present invention, the catalyst is prepared by mixing and heating one or more phosphorus containing compounds of formulae (IV) to (XXV) or their hydrated forms, and one or more nitrate salts of formulae (XXVI) to (XXVIII) or their hydrated forms. In another embodiment of the present invention, the catalyst is prepared by mixing and heating one or more phosphorus containing compounds of formula (IV) and one or more nitrate salts of formula (XXVII). In a further embodiment of the present invention, the catalyst is prepared by mixing and heating a phosphorus containing compound of formula (IV) wherein y is equal to 2, a phosphorus containing compound of formula (IV) wherein y is equal to 0 (i.e., phosphoric acid), and a nitrate salt of formula (XXVII). In yet another embodiment of the present invention, the catalyst is prepared by mixing and heating $K_2HPO_4$, $H_3PO_4$, and $Ba(NO_3)_2$. In yet another embodiment, the catalyst is prepared by mixing and heating $K_2HPO_4$, $H_3PO_4$, and $Ca(NO_3)_2$.

In one embodiment of the present invention, the catalyst is prepared by mixing and heating one or more phosphorus containing compounds of formula (IV) and one or more nitrate salts of formula (XXVIII). In a further embodiment of the present invention, the catalyst is prepared by mixing and heating a phosphorus containing compound of formula (IV) wherein y is equal to 2, a phosphorus containing compound of formula (IV) wherein y is equal to 0 (i.e., phosphoric acid), and a nitrate salt of formula (XXVIII). In yet another embodiment of the present invention, the catalyst is prepared by mixing and heating $K_2HPO_4$, $H_3PO_4$, and $Mn(NO_3)_2 \cdot 4H_2O$.

In one embodiment of the present invention, the catalyst is prepared by mixing and heating one or more phosphorus containing compounds of formula (V) and one or more nitrate salts of formula (XXVI). In another embodiment of the present invention, the catalyst is prepared by mixing and heating a phosphorus containing compound of formula (V) wherein y is equal to 2, a phosphorus containing compound of formula (V) wherein y is equal to 0 (i.e., phosphoric acid), and a nitrate salt of formula (XXVI). In yet another embodiment of the present invention, the catalyst is prepared by mixing and heating $BaHPO_4$, $H_3PO_4$, and $KNO_3$. In another embodiment, the catalyst is prepared by mixing and heating $CaHPO_4$, $H_3PO_4$, and $KNO_3$.

In one embodiment of this invention, the catalyst is prepared by mixing and heating one or more phosphorus containing compounds of formula (V), one or more phosphorus containing compounds of formula (XV), and one or more nitrate salts of formula (XXVI). In a further embodiment of this invention, the catalyst is prepared by mixing and heating a phosphorus containing compound of formula (V), wherein y is equal to 0 (i.e., phosphoric acid); a phosphorus containing compound of formula (XV), wherein v is equal to 2; and a nitrate salt of formula (XXVI). In another embodiment of the present invention, the catalyst is prepared by mixing and heating $H_3PO_4$, $Ca_2P_2O_7$, and $KNO_3$. In yet another embodiment, the catalyst is prepared by mixing and heating $H_3PO_4$, $Ba_2P_2O_7$, and $KNO_3$.

In another embodiment of this invention, the catalyst is prepared by mixing and heating one or more phosphorus containing compounds of formula (VI) and one or more nitrate salts of formula (XXVI). In another embodiment of this invention, the catalyst is prepared by mixing and heating a phosphorus containing compound of formula (VI), wherein y is equal to 3; a phosphorus containing compound of formula (VI), wherein y is equal to 0 (i.e., phosphoric acid); and a nitrate salt of formula (XXVI). In yet another embodiment of this invention, the catalyst is prepared by mixing and heating $MnPO_4 \cdot qH_2O$, $H_3PO_4$, and $KNO_3$.

In one embodiment of this invention, the catalyst is prepared by mixing and heating one or more phosphorus containing compounds of formula (IV), one or more phosphorus containing compounds of formula (IX), and one or more nitrate salts of formula (XXVII). In another embodiment of this invention, the catalyst is prepared by mixing and heating a phosphorus containing compound of formula (IV), wherein y is equal to 2; a phosphorus containing compound of formula (IV), wherein y is equal to 0 (i.e., phosphoric acid); a phosphorus containing compound of formula (IX), wherein a is equal to 2, b is equal to 1, and c is equal to 1; and a nitrate salt of formula (XXVII). In yet another embodiment of this invention, the catalyst is prepared by mixing and heating $K_2HPO_4$, $H_3PO_4$, $Cu_2(OH)PO_4$, and $Ba(NO_3)_2$.

In one embodiment of this invention, the catalyst is prepared by mixing and heating one or more phosphorus containing compounds of formula (V), one or more phosphorus containing compounds of formula (IX), and one or more nitrate salts of formula (XXVI). In another embodiment of this invention, the catalyst is prepared by mixing and heating a phosphorus containing compound of formula (V), wherein y is equal to 3; a phosphorus containing compound of formula (V), wherein y is equal to 0 (i.e., phosphoric acid); a phosphorus containing compound of formula (IX), wherein a is equal to 2, b is equal to 1, and c is equal to 1; and a nitrate salt of formula (XXVI). In yet another embodiment, the catalyst is prepared by mixing and heating $Ba_3(PO_4)_2$, $H_3PO_4$, $Cu_2(OH)PO_4$, and $KNO_3$.

In one embodiment of the present invention, the catalyst is prepared by mixing and heating one or more phosphorus containing compounds described by one of the formulae (IV) to (XXV) or any of the hydrated forms, and one or more carbonate salts described by one of the formulae (XXIX) to (XXXI) or any of the hydrated forms.

In one embodiment of the present invention, the catalyst is prepared by mixing and heating one or more phosphorus containing compounds described by one of the formulae (IV) to (XXV) or any of the hydrated forms, and one or more acetate salts described by one of the formulae (XXXII) to (XXXV), any other organic acid-derived salts, or any of the hydrated forms.

In one embodiment of the present invention, the catalyst is prepared by mixing and heating one or more phosphorus containing compounds described by one of the formulae (IV) to (XXV) or any of the hydrated forms, and one or more metal oxides described by one of the formulae (XXXVI) to (XXXIX) or any of the hydrated forms.

In one embodiment of the present invention, the catalyst is prepared by mixing and heating one or more phosphorus containing compounds described by one of the formulae (IV) to (XXV) or any of the hydrated forms, and one or more chloride salts described by one of the formulae (XXXX) to (XXXXIII), any other halide salts, or any of the hydrated forms.

In one embodiment of the present invention, the catalyst is prepared by mixing and heating one or more phosphorus containing compounds described by one of the formulae (IV) to (XXV) or any of the hydrated forms, and one or more sulfate salts described by one of the formulae (XXXXIV) to (XXXXVII) or any of the hydrated forms.

In one embodiment of the present invention, the catalyst is prepared by mixing and heating one or more phosphorus containing compounds described by one of the formulae (IV) to (XXV) or any of the hydrated forms, and one or more hydroxides described by one of the formulae (XXXXVIII) to (XL) or any of the hydrated forms.

In one embodiment of the present invention, the catalyst is prepared by mixing and heating one or more phosphorus containing compounds of formulae (IV) to (XXV), and two or more non-phosphorus containing compounds of formulae (XXVI) to (XL) or their hydrated forms.

In one embodiment, the molar ratio of phosphorus to the cations (i.e., $M^I + M^{II} + M^{III} + \ldots$) is between about 0.7 and about 1.7; in another embodiment, the molar ratio of phosphorus to the cations (i.e., $M_I + M_{II} + M^{III} + \ldots$) is between about 0.8 and about 1.3, and in yet another embodiment, the molar ratio of phosphorus to the cations (i.e., $M_I + M_{II} + M^{III} + \ldots$) is about 1. For example, in an embodiment when the catalyst includes potassium ($K^+$) and barium ($Ba^{2+}$), the molar ratio between phosphorus and the metals (K+Ba) is between about 0.7 and about 1.7; and in another embodiment, the molar ratio between phosphorus and the metals (K+Ba) is about 1 about 1.

When the catalyst includes only two different cations, the molar ratio between cations is, in one embodiment, between about 1:50 and about 50:1; and in another embodiment, the molar ratio between cations is between about 1:4 and about 4:1. For example, when the catalyst includes potassium ($K^+$) and barium ($Ba^{2+}$), the molar ratio between them (K:Ba), in one embodiment, is between about 1:4 and about 4:1. Also, when the catalyst is prepared by mixing and heating $K_2HPO_4$, $Ba(NO_3)_2$, and $H_3PO_4$, the potassium and barium are present, in another embodiment, in a molar ratio, K:Ba, between about 2:3 to about 1:1.

In one embodiment, the catalyst can include an inert support that is constructed of a material comprising silicates, aluminates, carbons, metal oxides, and mixtures thereof. Alternatively, the carrier is inert relative to the reaction mixture expected to contact the catalyst. In another embodiment, the method of preparing the catalyst can further include mixing an inert support with the catalyst before, during, or after the mixing and heating of the phosphorus containing compounds, wherein the inert support includes silicates, aluminates, carbons, metal oxides, and mixtures thereof. In yet another embodiment, the method of preparing the catalyst can further include mixing an inert support with the catalyst before, during, or after the mixing and heating of the phosphorus containing compounds and the non-phosphorus containing compounds, wherein the inert support includes silicates, aluminates, carbons, metal oxides, and mixtures thereof.

Mixing of the phosphorus containing compounds or the phosphorus containing and non-phosphorus containing compounds of the catalyst can be performed by any method known to those skilled in the art, such as, by way of example and not limitation: solid mixing and co-precipitation. In the solid mixing method, the various components are physically mixed together with optional grinding using any method known to those skilled in the art, such as, by way of example and not limitation, shear, extensional, kneading, extrusion, and others. In the co-precipitation method, an aqueous solution or suspension of the various components, including one or more of the phosphate compounds, is prepared, followed by optional filtration and heating to remove solvents and volatile materials (e.g., water, nitric acid, carbon dioxide, ammonia, or acetic acid). The heating is typically done using any method known to those skilled in the art, such as, by way of example and not limitation, convection, conduction, radiation, microwave heating, and others.

In one embodiment of the invention, the catalyst is calcined. Calcination is a process that allows chemical reaction and/or thermal decomposition and/or phase transition and/or removal of volatile materials. The calcination process is carried out with any equipment known to those skilled in the art, such as, by way of example and not limitation, furnaces or reactors of various designs, including shaft furnaces, rotary kilns, hearth furnaces, and fluidized bed reactors. The calcination temperature is, in one embodiment, about 200° C. to about 1200° C.; in another embodiment, the calcination temperature is about 250° C. to about 900° C.; and in yet another embodiment, the calcination temperature is about 300° C. to 600° C. The calcination time is, in one embodiment, about one hour to about seventy-two hours.

While many methods and machines are known to those skilled in the art for fractionating particles into discreet sizes and determining particle size distribution, sieving is one of the easiest, least expensive, and common ways. An alternative way to determine the size distribution of particles is with light scattering. Following calcination, the catalyst is, in one embodiment, ground and sieved to provide a more uniform product. The particle size distribution of the catalyst particles includes a particle span that, in one embodiment, is less than about 3; in another embodiment, the particle size distribution of the catalyst particles includes a particle span that is less than about 2; and in yet another embodiment, the particle size distribution of the catalyst particles includes a particle span that is less than about 1.5. In another embodiment of the invention, the catalyst is sieved to a median particle size of about 50 µm to about 500 µm. In another embodiment of the invention, the catalyst is sieved to a median particle size of about 100 pm to about 200 µm.

In another embodiment, the catalyst is prepared by the following steps, which comprise: (a) combining a phosphorus containing compound, a nitrate salt, phosphoric acid, and water to give a wet mixture, wherein the molar ratio between phosphorus and the cations is about 1, (b) calcining the wet mixture stepwise at about 50° C., about 80° C., about 120° C., and about 450° C. to about 550° C. to give a dried solid, and (c) grinding and sieving the dried solid to about 100 µm to about 200 µm, to produce the catalyst.

In another embodiment, the catalyst is prepared by the following steps, which comprise: (a) combining $MnPO_4 \cdot qH_2O$, $KNO_3$, and $H_3PO_4$, in a molar ratio of about 0.3:1:1, on an anhydrous basis, and water to give a wet mixture, (b) calcining the wet mixture stepwise at about 50° C., about 80° C., about 120° C., and about 450° C. to about 550° C. to give a dried solid, and (c) grinding and sieving the dried solid to about 100 µm to about 200 µm, to produce the catalyst.

In another embodiment, the catalyst is prepared by the following steps, which comprise: (a) combining $Ca_2P_2O_7$, $KNO_3$, and $H_3PO_4$, in a molar ratio of about 1.6:1:1, and water to give a wet mixture, (b) calcining the wet mixture stepwise at about 50° C., about 80° C., about 120° C., and about 450° C. to about 550° C. to give a dried solid, and (c) grinding and sieving the dried solid to about 100 µm to about 200 µm, to produce the catalyst.

In another embodiment, the catalyst is prepared by the following steps, which comprise: (a) combining a phosphorus containing compound, a nitrate salt, phosphoric acid, and water to form a wet mixture, wherein the molar ratio between phosphorus and the cations in both the phosphorus containing compound and nitrate salt is about 1, (b) heating the wet mixture to about 80° C. with stirring until near dryness to produce a wet solid, (c) calcining the wet solid stepwise at about 50° C., about 80° C., about 120° C., and about 450° C. to about 550° C. to give a dried solid, and (d) grinding and sieving the dried solid to about 100 µm to about 200 µm, to produce the catalyst.

In another embodiment, the catalyst is prepared by the following steps, which comprise: (a) combining $Ba(NO_3)_2$, $K_2HPO_4$, and $H_3PO_4$, in a molar ratio of about 3:1:4, and water to give a wet mixture, (b) heating the wet mixture to about 80° C. with stirring until near dryness to form a wet solid, (c) calcining the wet solid stepwise at about 50° C., about 80° C., about 120° C., and about 450° C. to about 550° C. to give a dried solid, and (d) grinding and sieving the dried solid to about 100 µm to about 200 µm, to produce the catalyst.

In another embodiment, the catalyst is prepared by the following steps, which comprise: (a) combining $Mn(NO_3)_2 \cdot 4H_2O$, $K_2HPO_4$, and $H_3PO_4$, in a molar ratio of about 1:1.5:2, and water to give a wet mixture, (b) heating the wet mixture to about 80° C. with stirring until near dryness to form a wet solid, (c) calcining the wet solid stepwise at about 50° C., about 80° C., about 120° C., and about 450° C. to about 550° C. to give a dried solid, and (d) grinding and sieving the dried solid to about 100 µm to about 200 µm, to produce the catalyst.

In another embodiment, the catalyst is prepared by the following steps, which comprise: (a) combining $Ca_2P_2O_7$ and $KH_2PO_4$ in a molar ratio of about 3:1 to give a solid mixture, and (b) calcining the solid mixture stepwise at about 50° C., about 80° C., about 120° C., and about 450° C. to about 550° C., to produce the catalyst.

Following calcination and optional grinding and sieving, the catalyst can be utilized to catalyze several chemical reactions. Non-limiting examples of reactions are: dehydration of hydroxypropionic acid to acrylic acid (as described in further detail below), dehydration of glycerin to acrolein, dehydration of aliphatic alcohols to alkenes or olefins, dehydrogenation of aliphatic alcohols to ethers, other dehydrogenations, hydrolyses, alkylations, dealkylations, oxidations, disproportionations, esterifications, cyclizations, isomerizations, condensations, aromatizations, polymerizations, and other reactions that may be apparent to those having ordinary skill in the art.

V Process for the Production of Acrylic Acid or its Derivatives from Hydroxypropionic Acid or its Derivatives A process for converting hydroxypropionic acid, hydroxypropionic acid derivatives, or mixtures thereof to acrylic acid, acrylic acid derivatives, or mixtures thereof of the present invention comprises the following steps: a) providing an aqueous solution comprising hydroxypropionic acid, hydroxypropionic acid derivatives, or mixtures thereof, wherein the hydroxypropionic acid is in monomeric form in the aqueous solution; b) combining the aqueous solution with an inert gas to form an aqueous solution/gas blend; c) evaporating the aqueous solution gas/blend to produce a gaseous mixture; and d) dehydrating the gaseous mixture by contacting the mixture with a dehydration catalyst under a pressure of at least about 80 psig.

Hydroxypropionic acid can be 3-hydroxypropionic acid, 2-hydroxypropionic acid (also called, lactic acid), 2-methyl hydroxypropionic acid, or mixtures thereof. Derivatives of hydroxypropionic acid can be metal or ammonium salts of hydroxypropionic acid, alkyl esters of hydroxypropionic acid, alkyl esters of 2-methyl hydroxypropionic acid, cyclic di-esters of hydroxypropionic acid, hydroxypropionic acid anhydride, or a mixture thereof. Non-limiting examples of metal salts of hydroxypropionic acid are sodium hydroxypropionate, potassium hydroxypropionate, and calcium hydroxypropionate. Non-limiting examples of alkyl esters of hydroxypropionic acid are methyl hydroxypropionate, ethyl hydroxypropionate, butyl hydroxypropionate, 2-ethylhexyl hydroxypropionate, or mixtures thereof. A non-limiting example of cyclic di-esters of hydroxypropionic acid is dilactide.

Hydroxypropionic acid can be in monomeric form or as oligomers in an aqueous solution of hydroxypropionic acid, hydroxypropionic acid derivatives, or mixtures thereof. In one embodiment, the oligomers of the hydroxypropionic acid in an aqueous solution of hydroxypropionic acid, hydroxypropionic acid derivatives, or mixtures thereof are less than about 25 wt % based on the total amount of hydroxypropionic acid, hydroxypropionic acid derivatives, or mixtures thereof. In another embodiment, the oligomers of the hydroxypropionic acid in an aqueous solution of hydroxypropionic acid, hydroxypropionic acid derivatives, or mixtures thereof are less than about 10 wt % based on the total amount of hydroxypropionic acid, hydroxypropionic acid derivatives, or mixtures thereof. In another embodiment, the oligomers of the hydroxypropionic acid in an aqueous solution of hydroxypropionic acid, hydroxypropionic acid derivatives, or mixtures thereof are less than about 5 wt % based on the total amount of hydroxypropionic acid, hydroxypropionic acid derivatives, or mixtures thereof. In yet another embodiment, the hydroxypropionic acid is in monomeric form in an aqueous solution of hydroxypropionic acid, hydroxypropionic acid derivatives, or mixtures thereof. The process steps to remove the oligomers from the aqueous solution can be purification or diluting with water and heating. In one embodiment, the heating step can involve heating the aqueous solution of hydroxypropionic acid, hydroxypropionic acid derivatives, or mixtures thereof at a temperature from about 50° C. to about 100° C. to remove the oligomers of the hydroxypropionic acid. In another embodiment, the heating step can involve heating the lactic acid aqueous solution at a temperature from about 95° C. to about 100° C. to remove the oligomers of the lactic acid and produce a monomeric lactic acid aqueous solution comprising at least 95 wt % of lactic acid in monomeric form based on the total amount of lactic acid. In another embodiment, an about 88 wt % lactic acid aqueous solution (e.g. from Purac Corp., Lincolnshire, Ill.) is diluted with water to form an about 20 wt % lactic acid aqueous solution, to remove the ester impurities that are produced from the intermolecular condensation reaction. These esters can result in loss of product due to their high boiling point and oligomerization in the evaporation stage of the process. Additionally, these esters can cause coking, catalyst deactivation, and reactor plugging. As the water content decreases in the aqueous solution, the loss of feed material to the catalytic reaction, due to losses in the evaporation step, increases.

In one embodiment, the hydroxypropionic acid is lactic acid or 2-methyl lactic acid. In another embodiment, the hydroxypropionic acid is lactic acid. Lactic acid can be L-lactic acid, D-lactic acid, or mixtures thereof. In one embodiment, the hydroxypropionic acid derivative is methyl lactate. Methyl lactate can be neat or in an aqueous solution.

Acrylic acid derivatives can be metal or ammonium salts of acrylic acid, alkyl esters of acrylic acid, acrylic acid oligomers, or a mixture thereof. Non-limiting examples of metal salts of acrylic acid are sodium acrylate, potassium acrylate, and calcium acrylate. Non-limiting examples of alkyl esters of acrylic acid are methyl acrylate, ethyl acrylate, butyl acrylate, 2-ethylhexyl acrylate, or mixtures thereof.

In one embodiment, the concentration of the hydroxypropionic acid, hydroxypropionic acid derivatives, or mixtures thereof in the aqueous solution is between about 5 wt % and about 50 wt %. In another embodiment, the concentration of the hydroxypropionic acid, hydroxypropionic acid derivatives, or mixtures thereof in the aqueous solution is between about 10 wt % and about 25 wt %. In yet another embodiment, the concentration of the hydroxypropionic acid, hydroxypropionic acid derivatives, or mixtures thereof in the aqueous solution is about 20 wt %.

The aqueous solution can be combined with an inert gas to form an aqueous solution/gas blend. Non-limiting examples of the inert gas are air, nitrogen, helium, argon, carbon dioxide, carbon monoxide, steam, and mixtures thereof. The inert gas can be introduced to the evaporating step separately or in combination with the aqueous solution. The aqueous solution can be introduced with a simple tube or through atomization nozzles. Non-limiting examples of atomization nozzles include fan nozzles, pressure swirl atomizers, air blast atomizers, two-fluid atomizers, rotary atomizers, and supercritical carbon dioxide atomizers. In one embodiment, the droplets of the aqueous solution are less than about 500 µm in diameter. In another embodiment, the droplets of the aqueous solution are less than about 200 µm in diameter. In yet another embodiment, the droplets of the aqueous solution are less than about 100 µm in diameter.

In the evaporating step, the aqueous solution/gas blend is heated to give a gaseous mixture. In one embodiment, the temperature during the evaporating step is from about 165° C. to about 450° C. In another embodiment, the temperature during the evaporating step is from about 250° C. to about 375° C. In one embodiment, the gas hourly space velocity (GHSV) in the evaporating step is from about 720 $h^{-1}$ to 3,600 $h^{-1}$. In another embodiment, the gas hourly space velocity (GHSV) in the evaporating step is about 7,200 $h^{-1}$. The evaporating step can be performed at either atmospheric pressure or higher pressure. In one embodiment, the evaporating step is performed under a pressure from about 80 psig to about 550 psig. In another embodiment, the evaporating step is performed under a pressure from about 300 psig to about 400 psig. In yet another embodiment, the evaporating step is performed under a pressure from about 350 psig to about 375 psig. In one embodiment, the gaseous mixture comprises from about 0.5 mol % to about 50 mol % hydroxypropionic acid, hydroxypropionic acid derivatives, or mixtures thereof. In another embodiment, the gaseous mixture comprises from about 1 mol % to about 10 mol % hydroxypropionic acid, hydroxypropionic acid derivatives, or mixtures thereof. In another embodiment, the gaseous mixture comprises from about 1.5 mol % to about 3.5 mol % hydroxypropionic acid, hydroxypropionic acid derivatives, or mixtures thereof. In another embodiment, the gaseous mixture comprises about 2.5 mol % hydroxypropionic acid, hydroxypropionic acid derivatives, or mixtures thereof.

The evaporating step can be performed in various types of equipment, such as, but not limited to, plate heat exchanger, empty flow reactor, and fixed bed flow reactor. Regardless of the type of the reactor, in one embodiment, the reactor has an interior surface comprising material selected from the group consisting of quartz, borosilicate glass, silicon, hastelloy, inconel, manufactured sapphire, stainless steel, and mixtures thereof. In another embodiment, the reactor has an interior surface comprising material selected from the group consisting of quartz, borosilicate glass, and mixtures thereof. The evaporating step can be performed in a reactor with the aqueous solution flowing down, or flowing up, or flowing horizontally. In one embodiment, the evaporating step is performed in a reactor with the aqueous solution flowing down. Also, the evaporating step can be done in a batch form.

The gaseous mixture from the evaporating step is converted to acrylic acid, acrylic acid derivatives, and mixture thereof by contact it with a dehydration catalyst in the dehydrating step. The dehydration catalyst can be selected from the group comprising sulfates, phosphates, metal oxides, aluminates, silicates, aluminosilicates (e.g., zeolites), arsenates, nitrates, vanadates, niobates, tantalates, selenates, arsenatophosphates, phosphoaluminates, phosphoborates, phosphocromates, phosphomolybdates, phosphosilicates, phosphosulfates, phosphotungstates, and mixtures thereof, and others that may be apparent to those having ordinary skill in the art. The catalyst can contain an inert support that is constructed of a material comprising silicates, aluminates, carbons, metal oxides, and mixtures thereof. In one embodiment, the dehydrating step is performed in a reactor, wherein the reactor has an interior surface comprising material selected from the group consisting of quartz, borosilicate glass, silicon, hastelloy, inconel, manufactured sapphire, stainless steel, and mixtures thereof. In another embodiment, the dehydrating step is performed in a reactor, wherein the reactor has an interior surface comprising material selected from the group consisting of quartz, borosilicate glass, and mixtures thereof. In one embodiment, the temperature during the dehydrating step is from about 150° C. to about 500° C. In another embodiment, the temperature during the dehydrating step is from about 300° C. to about 450° C. In one embodiment, the GHSV in the dehydrating step is from about 720 h$^{-1}$ to about 36,000 h$^{-1}$. In another embodiment, the GHSV in the dehydrating step is about 3,600 h$^{-1}$. The dehydrating step can be performed at higher than atmospheric pressure. In one embodiment, the dehydrating step is performed under a pressure of at least about 80 psig. In another embodiment, the dehydrating step is performed under a pressure from about 80 psig to about 550 psig. In another embodiment, the dehydrating step is performed under a pressure from about 150 psig to about 500 psig. In yet another embodiment, the dehydrating step is performed under a pressure from about 300 psig to about 400 psig. The dehydrating step can be performed in a reactor with the gaseous mixture flowing down, flowing up, or flowing horizontally. In one embodiment, the dehydrating step is performed in a reactor with the gaseous mixture flowing down. Also, the dehydrating step can be done in a batch form.

In one embodiment, the evaporating and dehydrating steps are combined in a single step. In another embodiment, the evaporating and dehydrating steps are performed sequentially in a single reactor. In yet another embodiment, the evaporating and dehydrating steps are performed sequentially in a tandem reactor.

In one embodiment, the selectivity of acrylic acid, acrylic acid derivatives, and mixture thereof from hydroxypropionic acid, hydroxypropionic acid derivatives, or mixtures thereof is at least about 50%. In another embodiment, the selectivity of acrylic acid, acrylic acid derivatives, and mixture thereof from hydroxypropionic acid, hydroxypropionic acid derivatives, or mixtures thereof is at least about 80%. In one embodiment, the selectivity of propanoic acid from hydroxypropionic acid, hydroxypropionic acid derivatives, or mixtures thereof is less than about 5%. In another embodiment, the selectivity of propanoic acid from hydroxypropionic acid, hydroxypropionic acid derivatives, or mixtures thereof is less than about 1%. In one embodiment, the conversion of the hydroxypropionic acid, hydroxypropionic acid derivatives, or mixtures thereof is more than about 50%. In another embodiment, the conversion of the hydroxypropionic acid, hydroxypropionic acid derivatives, or mixtures thereof is more than about 80%.

In another embodiment of the present invention, a process for converting hydroxypropionic acid, hydroxypropionic acid derivatives, or mixtures thereof to acrylic acid, acrylic acid derivatives, or mixtures thereof is provided. The process comprises the following steps: a) providing an aqueous solution comprising hydroxypropionic acid, hydroxypropionic acid derivatives, or mixtures thereof, wherein the hydroxypropionic acid comprises oligomers in the aqueous solution; b) heating the aqueous solution at a temperature from about 50° C. to about 100° C. to remove the oligomers of the hydroxypropionic acid and produce an aqueous solution of monomeric hydroxypropionic acid; c) combining the aqueous solution of monomeric hydroxypropionic acid with an inert gas to form an aqueous solution/gas blend; d) evaporating the aqueous solution gas/blend to produce a gaseous mixture; and e) dehydrating the gaseous mixture by contacting the mixture with a dehydration catalyst and producing the acrylic acid, acrylic acid derivatives, or mixtures thereof.

In one embodiment, after the heating step, the concentration of the oligomers of the hydroxypropionic acid in the aqueous solution of monomeric of monomeric hydroxypropionic acid is less than about 20 wt % based on the total amount of hydroxypropionic acid, hydroxypropionic acid derivatives, or mixtures thereof. In another embodiment, after the heating step, the concentration of the oligomers of the hydroxypropionic acid in the aqueous solution of monomeric of monomeric hydroxypropionic acid is less than about 5 wt % based on the total amount of hydroxypropionic acid, hydroxypropionic acid derivatives, or mixtures thereof.

In another embodiment of the present invention, a process for converting hydroxypropionic acid, hydroxypropionic acid derivatives, or mixtures thereof to acrylic acid, acrylic acid derivatives, and mixture thereof is provided. The process comprises the following steps: a) providing an aqueous solution comprising hydroxypropionic acid, hydroxypropionic acid derivatives, or mixtures thereof, wherein the hydroxypropionic acid is in monomeric form in the aqueous solution; b) combining the aqueous solution with an inert gas to form an aqueous solution/gas blend; c) evaporating the aqueous solution/gas blend to produce a gaseous mixture; d) dehydrating the gaseous mixture by contacting the mixture with a dehydration catalyst producing acrylic acid, and/or acrylates; and e) cooling the acrylic acid, acrylic acid derivatives, and mixture thereof at a GHSV of more than about 360 $h_{-1}$.

The stream of acrylic acid, acrylic acid derivatives, and mixture thereof produced in the dehydrating step is cooled to give an aqueous acrylic acid composition as the product stream. The time required to cool stream of the acrylic acid, acrylic acid derivatives, or mixtures thereof must be controlled to reduce the decomposition of acrylic acid to ethylene and polymerization. In one embodiment, the GHSV of the acrylic acid, acrylic acid derivatives, and mixture thereof in the cooling step is more than about 720 $h^{-1}$.

In another embodiment of the present invention, a process for converting lactic acid to acrylic acid is provided. The process comprises the following steps: a) diluting an about 88 wt % lactic acid aqueous solution with water to form an about 20 wt % lactic acid aqueous solution; b) heating the about 20 wt % lactic acid aqueous solution at a temperature of about 95° C. to about 100° C. to remove oligomers of the lactic acid, producing a monomeric lactic acid solution comprising at least about 95 wt % of the lactic acid in monomeric form based on the total amount of lactic acid; c) combining the monomeric lactic acid solution with nitrogen to form an aqueous solution/gas blend; d) evaporating the aqueous solution/gas blend in a reactor with inside surface of borosilicate glass at a GHSV of about 7,200 $h^{-1}$ at a temperature from about 300° C. to about 350° C. to produce a gaseous mixture comprising about 2.5 mol % lactic acid and about 50 mol % water; e) dehydrating the gaseous mixture in a reactor with inside surface of borosilicate glass at a GHSV of about 3,600 $h^{-1}$ at a temperature of 350° C. to about 425° C. by contacting the mixture with a dehydration catalyst under a pressure of about 360 psig, producing the acrylic acid; and f) cooling the acrylic acid at a GHSV from about 360 $h^{-1}$ to about 36,000 $h^{-1}$.

In another embodiment of the present invention, a process for converting hydroxypropionic acid, derivatives of hydroxypropionic acid, and mixtures thereof to acrylic acid, acrylic acid derivatives, or mixtures thereof is provided. The process comprises the following steps: a) providing an aqueous solution comprising hydroxypropionic acid, hydroxypropionic acid derivatives, or mixtures thereof, wherein the hydroxypropionic acid is in monomeric form in the aqueous solution, and wherein the hydroxypropionic acid, hydroxypropionic acid derivatives, or mixtures thereof comprise from about 10 wt % to about 25 wt % of the aqueous solution; b) combining the aqueous solution with an inert gas to form an aqueous solution/gas blend; c) evaporating the aqueous solution/gas blend to produce a gaseous mixture; and d) dehydrating the gaseous mixture by contacting the mixture with a dehydration catalyst producing acrylic acid, acrylic acid derivatives, or mixtures thereof.

In another embodiment of the present invention, a process for converting alkyl lactates to acrylic acid, acrylic acid derivatives, or mixtures thereof is provided. The process comprises the following steps: a) providing alkyl lactates or a solution comprising alkyl lactates and a solvent; b) combining the alkyl lactates or the solution comprising the alkyl lactates and the solvent with an inert gas to form a liquid/gas blend; c) evaporating the liquid/gas blend to produce a gaseous mixture; and d) dehydrating the gaseous mixture by contacting the gaseous mixture with a dehydration catalyst under a pressure of at least about 80 psig, producing acrylic acid, acrylic acid derivatives, or mixtures thereof.

In one embodiment, alkyl lactates are selected from the group consisting of methyl lactate, ethyl lactate, butyl lactate, 2-ethylhexyl lactate, and mixtures thereof. In another embodiment, the solvent is selected from the group consisting of water, methanol, ethanol, butanol, 2-ethylhexanol, isobutanol, isooctyl alcohol, and mixtures thereof.

In another embodiment, a process for converting hydroxypropionic acid, hydroxypropionic acid derivatives, or mixtures thereof to acrylic acid, acrylic acid derivatives, or mixtures thereof is provided comprising the following steps: a) providing a solution comprising hydroxypropionic acid, hydroxypropionic acid derivatives, or mixtures thereof; b) combining the solution with a gas to form a solution/gas blend; and c) dehydrating the solution/gas blend by contacting the solution/gas blend with a dehydration catalyst.

VI Purification of Bio-Based Acrylic Acid to Crude and Glacial Acrylic Acid

In one embodiment, a glacial acrylic acid composition is provided comprising at least about 98 wt % acrylic acid, and wherein a portion of the remaining impurities in the glacial acrylic acid composition is hydroxypropionic acid, hydroxypropionic acid derivatives, or mixtures thereof.

In one embodiment, a crude acrylic acid composition is provided comprising between about 94 wt % and about 98 wt % acrylic acid, and wherein a portion of the remaining impurities in the glacial acrylic acid composition is hydroxypropionic acid, hydroxypropionic acid derivatives, or mixtures thereof.

Hydroxypropionic acid can be 3-hydroxypropionic acid, 2-hydroxypropionic acid (also called, lactic acid), 2-methyl hydroxypropionic acid, or mixtures thereof. Derivatives of hydroxypropionic acid can be metal or ammonium salts of hydroxypropionic acid, alkyl esters of hydroxypropionic acid, alkyl esters of 2-methyl hydroxypropionic acid, cyclic di-esters of hydroxypropionic acid, hydroxypropionic acid anhydride, or a mixture thereof. Non-limiting examples of metal salts of hydroxypropionic acid are sodium hydroxypropionate, potassium hydroxypropionate, and calcium hydroxypropionate. Non-limiting examples of alkyl esters of hydroxypropionic acid are methyl hydroxypropionate, ethyl hydroxypropionate, butyl hydroxypropionate, 2-ethylhexyl hydroxypropionate, or mixtures thereof. A non-limiting example of cyclic di-esters of hydroxypropionic acid is dilactide.

In one embodiment, the hydroxypropionic acid is lactic acid or 2-methyl lactic acid. In another embodiment, the hydroxypropionic acid is lactic acid. Lactic acid can be L-lactic acid, D-lactic acid, or mixtures thereof. In one embodiment, the hydroxypropionic acid, hydroxypropionic acid derivatives, or mixtures thereof in the impurities in the glacial acrylic acid composition are lactic acid, lactic acid derivatives, or mixtures thereof. In another embodiment, the hydroxypropionic acid, hydroxypropionic acid derivatives, or mixtures thereof in the impurities in the crude acrylic acid composition are lactic acid, lactic acid derivatives, or mixtures thereof.

In one embodiment, the concentration of the hydroxypropionic acid, hydroxypropionic acid derivatives, or mixtures thereof in the remaining impurities of the glacial acrylic acid composition is less than about 2 wt %, based on the total amount of the glacial acrylic acid composition. In another embodiment, the hydroxypropionic acid, hydroxypropionic acid derivatives, or mixtures thereof in the remaining impurities of the glacial acrylic acid composition is less than about 1 wt %, based on the total amount of the glacial acrylic acid composition. In another embodiment, the hydroxypropionic acid, hydroxypropionic acid derivatives, or mixtures thereof in the remaining impurities of the glacial acrylic acid composition is less than about 400 ppm, based on the total amount of the glacial acrylic acid composition.

In one embodiment, the bio-based content of the glacial acrylic acid is greater than about 3%. In another embodiment, the bio-based content of the glacial acrylic acid is greater than 30%. In yet another embodiment, the bio-based content of the glacial acrylic acid is greater than about 90%. In one embodiment, the bio-based content of the crude acrylic acid is greater than about 3%. In another embodiment, the bio-based content of the crude acrylic acid is greater than 30%. In yet another embodiment, the bio-based content of the crude acrylic acid is greater than about 90%.

The glacial or crude acrylic acid composition can be made from an aqueous solution of acrylic acid produced from renewable resources or materials and fed into the purification process to produce crude acrylic acid or glacial acrylic acid. Non-limiting examples of renewable resources or materials for the production of the aqueous solution of acrylic acid are hydroxypropionic acid, hydroxypropionic acid derivatives, or mixtures thereof; glycerin; carbon monoxide and ethylene oxide; carbon dioxide and ethylene; and crotonic acid. In one embodiment, the renewable resources or materials are hydroxypropionic acid, hydroxypropionic acid derivatives, or mixtures thereof. In another embodiment, the renewable resources or materials are lactic acid, lactic acid derivatives, or mixtures thereof. In yet another embodiment, the renewable resource or material is lactic acid.

In one embodiment, the aqueous solution of acrylic acid comprises: 1) acrylic acid; 2) lactic acid, lactic acid derivatives, or mixtures thereof, and is essentially free of maleic anhydride, furfural, and formic acid. In another embodiment, the aqueous solution of acrylic acid has from about 4 wt % to about 80 wt % acrylic acid. In another embodiment, the aqueous solution of acrylic acid has from about 4 wt % to about 40 wt % acrylic acid. In yet another embodiment, the aqueous solution of acrylic acid has from about 5 wt % to about 25 wt % acrylic acid. In another embodiment, the aqueous solution of acrylic acid has from about 8 wt % to about 16 wt % acrylic acid.

In one embodiment, the aqueous solution of acrylic acid has from about 0.001 wt % to about 50 wt % lactic acid, lactic acid derivatives, or mixtures thereof. In another embodiment, the aqueous solution of acrylic acid has from about 0.001 wt % to about 20 wt % % lactic acid, lactic acid derivatives, or mixtures thereof. In yet another embodiment, the aqueous solution of acrylic acid has about 6 wt % % lactic acid, lactic acid derivatives, or mixtures thereof.

In one embodiment, the aqueous solution of acrylic acid has from about 8 wt % to about 16 Wt % acrylic acid and from about 0.1 wt % to about 10 wt % lactic acid, lactic acid derivatives, or mixtures thereof, and wherein the aqueous solution of acrylic acid is essentially free of maleic anhydride, furfural, and formic acid. Non-limiting examples of impurities that can be present in the aqueous solution of acrylic acid are acetaldehyde, acetic acid, and propanoic acid.

The aqueous solution of acrylic acid can be extracted with a solvent to produce an extract. In one embodiment, the solvent is selected from the group consisting of ethyl acetate, isobutyl acetate, methyl acetate, toluene, dimethyl phthalate, hexane, pentane, diphenyl ether, ethyl hexanoic acid, N-methylpyrrolidone, C6 to C10 paraffin fractions, and mixtures thereof. In another embodiment, the extraction solvent is ethyl acetate. In one embodiment, the extraction solvent can form an azeotrope with water.

In one embodiment, the solvent comprises at least one polymerization inhibitor. Non-limiting examples of polymerization inhibitors are phenothiazine and 4-methoxy phenol. In another embodiment, the glacial acrylic acid comprises from about 200 ppm to about 400 ppm 4-methoxyphenol. In another embodiment, the polymerization inhibitor is added to the aqueous solution of acrylic acid before the extracting step.

After the extraction, the extract can be dried to produce a dried extract. The drying can be achieved with a variety of methods, such as, and not by way of limitation, distillation and sorption. In one embodiment, the drying is performed by azeotropic distillation. In another embodiment, the sorption is performed on a solid powder. In yet another embodiment, the solid powder is selected from the group consisting of magnesium sulfate, sodium sulfate, calcium sulfate, molecular sieves, metal hydrides, reactive metals, and mixtures thereof. In yet another embodiment, the sorption is performed with sodium sulfate and is followed by filtration to produce a dried filtrate.

The dried extract or dried filtrate can be further processed by distillation to produce a distilled acrylic acid composition. In one embodiment, the distillation is vacuum distillation at about 70 mm Hg and about 40° C. to produce a distilled crude acrylic acid composition, and is followed by a fractional distillation at about 40 mm Hg and collecting fractions from 59° C. to 62° C. to produce the distilled acrylic acid composition.

In one embodiment, cooling of the distilled acrylic acid composition to a temperature from about −21° C. to about 14° C. produces crystals of acrylic acid; partially melting the crystals of acrylic acid produces a liquid/solid mixture; decanting the liquid/solid mixture produces a purified acrylic acid solid composition; fully melting the purified acrylic acid solid composition produces a purified acrylic acid liquid composition; and determining acrylic acid purity of the purified acrylic acid liquid composition, and if the purity is less than about 98 wt % acrylic acid, repeating the cooling, partially melting, decanting, and fully melting steps on the purified acrylic acid liquid composition until a purity of about 98 wt % acrylic acid is achieved and a glacial acrylic acid composition is produced.

In another embodiment, cooling of the distilled acrylic acid composition to a temperature from about −21° C. to about 14° C. produces crystals of acrylic acid; partially melting the crystals of acrylic acid produces a liquid/solid mixture; decanting the liquid/solid mixture produces a purified acrylic acid solid composition; fully melting the purified acrylic acid solid composition produces a purified acrylic acid liquid composition; and determining acrylic acid purity of the purified acrylic acid liquid composition, and if the purity is less than about 94 wt % acrylic acid, repeating the cooling, partially melting, decanting, and fully melting steps on the purified acrylic acid liquid composition until a purity of about 94 wt % acrylic acid is achieved and a crude acrylic acid composition is produced.

In yet another embodiment, cooling of the distilled acrylic acid composition to a temperature from about −21° C. to about 14° C. produces crystals of acrylic acid; partially melting the crystals of acrylic acid produces a liquid/solid mixture; decanting the liquid/solid mixture produces a purified acrylic acid solid composition; fully melting the purified acrylic acid solid composition produces a purified acrylic acid liquid composition; and determining acrylic acid purity of the purified acrylic acid liquid composition, and if the purity is less than about 99 wt % acrylic acid, repeating the cooling, partially melting, decanting, and fully melting steps on the purified acrylic acid liquid composition until a purity of about 99 wt % acrylic acid is achieved and a glacial acrylic acid composition is produced.

In one embodiment, the distilling step is followed by determining the acrylic acid purity of the distilled acrylic acid composition, and if the purity is less than about 98 wt % acrylic acid, repeating the distilling step on the purified acrylic acid composition until a purity of about 98 wt % acrylic acid is achieved and a glacial acrylic acid composition is produced. In another embodiment, the distilling step is followed by determining the acrylic acid purity of the distilled acrylic acid composition, and if the purity is less than about 94 wt % acrylic acid, repeating the distilling step on the purified acrylic acid composition until a purity of about 94 wt % acrylic acid is achieved and a crude acrylic acid composition is produced.

In one embodiment, the distilled acrylic acid composition is cooled to a temperature from about 0° C. to about 5° C. to produce crystals of acrylic acid.

In one embodiment of the present invention, the glacial acrylic acid composition is produced by the steps comprising: a) providing an aqueous solution of acrylic acid comprising 1) acrylic acid and 2) lactic acid, lactic acid derivatives, or mixtures thereof, and wherein the aqueous solution of acrylic acid is essentially free of maleic anhydride, furfural, and formic acid; b) extracting the aqueous solution of acrylic acid with a solvent to produce an extract; c) drying the extract to produce a dried extract; d) distilling the dried extract to produce crude acrylic acid; e) cooling the crude acrylic acid to a temperature from about −21° C. to about 14° C. to produce crystals of acrylic acid; f) partially melting the crystals of acrylic acid to produce a liquid/solid mixture; g) decanting the liquid/solid mixture to produce a acrylic acid solid composition; h) fully melting the purified acrylic acid solid composition to produce a purified acrylic acid composition; and i) determining the acrylic acid purity of the purified acrylic acid liquid composition and if the purity is less than 98 wt % acrylic acid repeating the cooling, partially melting, decanting, and fully melting steps on the purified acrylic acid liquid composition until a purity of about 98 wt % is achieved to produce glacial acrylic acid composition.

In another embodiment of the present invention, a glacial acrylic acid composition is provided produced by the steps comprising: a) providing an aqueous solution of acrylic acid comprising: 1) acrylic acid; and 2) lactic acid, lactic acid derivatives, or mixtures thereof, and wherein the aqueous solution of acrylic acid is essentially free of maleic anhydride, furfural, and formic acid; b) extracting the aqueous solution of acrylic acid with a solvent to produce an extract; c) drying the extract to produce a dried extract; d) distilling the dried extract to produce a distilled acrylic acid composition; and e) determining the acrylic acid purity of the distilled acrylic acid composition, and if the purity is less than about 98 wt % acrylic acid, repeating the distilling step on the purified acrylic acid composition until a purity of about 98 wt % acrylic acid is achieved and the glacial acrylic acid composition is produced.

In one embodiment of the present invention, a crude acrylic acid composition is provided produced by the steps comprising: a) providing an aqueous solution of acrylic acid comprising: 1) acrylic acid; and 2) lactic acid, lactic acid derivatives, or mixtures thereof, and wherein the aqueous solution of acrylic acid is essentially free of maleic anhydride, furfural, and formic acid; b) extracting the aqueous solution of acrylic acid with a solvent to produce an extract; c) drying the extract to produce a dried extract; d) distilling the dried extract to produce a distilled acrylic acid composition; and e) determining the acrylic acid purity of the distilled acrylic acid composition, and if the purity is less than about 94 wt % acrylic acid, repeating the distilling step on the purified acrylic acid composition until a purity of about 94 wt % acrylic acid is achieved and the crude acrylic acid composition is produced.

In another embodiment of the present invention, a crude acrylic acid composition is provided produced by the steps comprising: a) providing an aqueous solution of acrylic acid comprising: 1) acrylic acid; and 2) lactic acid, lactic acid derivatives, or mixtures thereof, and wherein the aqueous solution of acrylic acid is essentially free of maleic anhydride, furfural, and formic acid; b) extracting the aqueous solution of acrylic acid with a solvent to produce an extract; c) drying the extract to produce a dried extract; d) distilling the dried extract to produce a distilled acrylic acid composition; e) cooling the distilled acrylic acid composition to a temperature from about −21° C. to about 14° C. to produce crystals of acrylic acid; f) partially melting the crystals of acrylic acid to produce a liquid/solid mixture; g) decanting the liquid/solid mixture to produce a purified acrylic acid solid composition; h) fully melting the purified acrylic acid solid composition to produce a purified acrylic acid liquid composition; and i) determining the acrylic acid purity of the purified acrylic acid liquid composition, and if the purity is less than about 94 wt % acrylic acid, repeating the cooling, partially melting, decanting, and fully melting steps on the purified acrylic acid liquid composition until a purity of about 94 wt % acrylic acid is achieved and the crude acrylic acid composition is produced.

In one embodiment of the present invention, a glacial acrylic acid composition is provided comprising about 99 wt % acrylic acid, produced by the steps comprising: a) providing an aqueous solution of acrylic acid comprising: 1) from about 8 wt % to about 16 wt % acrylic acid; and 2) from about 0.1 wt % to about 10 wt % lactic acid, lactic acid derivatives, or mixtures thereof, and wherein the aqueous solution of acrylic acid is essentially free of maleic anhydride, furfural, and formic acid; b) extracting the aqueous solution of acrylic acid, with ethyl acetate to produce an extract; c) drying the extract with sodium sulfate to produce a dried extract; d) vacuum distilling the dried extract at about 70 mm Hg and 40° C. to produce a distilled crude acrylic acid composition; e) fractionally distilling the distilled crude acrylic acid composition at about 40 mm Hg and collecting fractions from 59° C. to 62° C. to produce a distilled acrylic acid composition; f) cooling the distilled acrylic acid composition to a temperature from about 0° C. to about 5° C. to produce crystals of acrylic acid; g) partially melting the crystals of acrylic acid to produce a liquid/solid mixture; h) decanting the liquid/solid mixture to produce a purified acrylic acid solid composition; i) fully melting the purified acrylic acid composition to produce a purified acrylic acid liquid composition; and j) determining the acrylic acid purity of the purified acrylic acid liquid composition, and if the purity is less than about 99 wt % acrylic acid, repeating the cooling, partially melting, decanting, and fully melting steps on the purified acrylic acid liquid composition until a purity of about 99 wt % acrylic acid is achieved and the glacial acrylic acid composition is produced.

VII Examples

The following examples are provided to illustrate the invention, but are not intended to limit the scope thereof.

Example 1

Solid dibasic potassium phosphate, $K_2HPO_4$ (36.40 g, 209 mmol, ≥98%; Sigma—Aldrich Co., St. Louis, Mo.; catalog

P3786) was mixed quickly with an aqueous solution of barium nitrate, $Ba(NO_3)_2$ (2050 mL of a 0.08 g/mL stock solution, 627 mmol, 99.999%; Sigma—Aldrich Co., St. Louis, Mo.; catalog #202754) at room temperature. Phosphoric acid, $H_3PO_4$ (58.7 mL of an 85 wt %, density=1.684 g/mL, 857 mmol; Acros Organics, Geel, Belgium; catalog #295700010), was added to the slurry, providing a solution containing potassium ($K^+$, $M^I$) and Barium ($Ba^{2+}$, $M^{II}$) cations. The final pH of the suspension was about 1.6. The acid-containing suspension was then dried slowly in a glass beaker at 80° C. using a heating plate while magnetically stirring the suspension until the liquid was evaporated and the material was almost completely dried. Heating was continued in a oven with air circulation (G1530A, HP6890 GC; Agilent Corp., Santa Clara, Calif.) at 50° C. for 5.3 h, then at 80° C. for 10 h (0.5° C./min ramp), following by cooling down at 25° C. The material was calcined at 120° C. for 2 hours (0.5° C./min ramp) followed by 450° C. for 4 hours (2° C./min ramp) using the same oven. After calcination, the material was left inside the oven until it cooled down by itself at a temperature below 25° C. before it was taken out of the oven. Finally, the catalyst was ground and sieved to about 100 μm to about 200 μm.

Example 2

454 g of an 88 wt % L-lactic acid solution (Purac Corp., Lincolnshire, Ill.) was diluted with 1,300 g of water. The diluted solution was heated to 95° C. and held at that temperature with stirring for about 4 to 12 hours. Then, the solution was cooled to room temperature, and its lactic acid and lactic acid oligomers concentrations were measured by HPLC (Agilent 1100 system; Santa Clara, Calif.) equipped with a DAD detector and a Waters Atlantis T3 column (Catalog #186003748; Milford, Mass.) using methods generally known by those having ordinary skill in the art. The solution was essentially free of oligomers. Finally, the solution was further diluted with water to yield a 20 wt % L-lactic acid aqueous solution and essentially free of oligomers.

Example 3

The reactor consisted of an electric clam shell furnace (Applied Test systems, Butler, Pa.) with an 8" (20.3 cm) heated zone with one temperature controller connected in series to another electric clam shell furnace (Applied Test Systems, Butler, Pa.) with a 16" (40.6 cm) heated zone containing two temperature controllers and a reactor tube. The reactor tube consisted of a 13" (33 cm) borosilicate glass-lined tube (SGE Analytical Science Pty Ltd., Ringwood, Australia)) and a 23" (58.4 cm) borosilicate glass lined tube connected in series using a Swagelok™ tee fitting equipped with an internal thermocouple and having an inside diameter of 9.5 mm. The head of the column was fitted with a ⅛" (3.2 mm) stainless steel nitrogen feed line and a 1/16" (1.6 mm) fused silica lined stainless steel liquid feed supply line connected to a HPLC pump (Smartline 100, Knauer, Berlin, Germany) that was connected to a lactic acid feed tank. The bottom of the reactor was connected to a Teflon-lined catch tank using ⅛" (3.2 mm) fused silica lined stainless steel tubing and Swagelok∩ fittings. The reactor column was packed with a plug of glass wool, 13 g of fused quartz, 16" (40.7 cm) with catalyst of Example 1 (47 g and 28.8 mL packed bed volume) and topped with 25 g of fused quartz. The reactor tube was placed in an aluminum block and placed into the reactor from above in a downward flow. The reactor was preheated to 375° C. overnight under 0.25 L/min nitrogen. The nitrogen feed was increased to 0.85 L/min during the experiment. The liquid feed was a 20 wt % aqueous solution of L-lactic acid, prepared as in Example 2, and fed at 0.845 mL/min (LHSV of 1.8 $h^-$; 50.7 g/h), giving a residence time of about 1 s (GHSV of 3,600 $h^{-1}$) at STP conditions. The clam shell heaters were adjusted to give an internal temperature about 350° C. After flowing through the reactor, the gaseous stream was cooled and the liquid was collected in the catch tank for analysis by off-line HPLC using an Agilent 1100 system (Santa Clara, Calif.) equipped with a DAD detector and a Waters Atlantis T3 column (Catalog #186003748; Milford, Mass.) using methods generally known by those having ordinary skill in the art. The gaseous stream was analyzed on-line by GC using an Agilent 7890 system (Santa Clara, Calif.) equipped with a FID detector and Varian CP-Para Bond Q column (Catalog # CP7351; Santa Clara, Calif.). The crude reaction mixture was cooled and collected over 159 h to give 748 g acrylic acid as a crude mixture in 54% yield, 75% acrylic acid selectivity, and 69% conversion of lactic acid. The acrylic acid yield, corrected for the losses during the evaporating step, was 61% and its selectivity was 89%. The acrylic acid aqueous concentration was 8.4 wt %, and that of lactic acid was 6.3 wt %.

Example 4

The reaction mixtures from Example 3 were combined into four batches and isolated to give an acrylic acid solution of 668.9 g of acrylic acid in water. A stabilizer (200-400 ppm phenothiazine) was added to each batch and the batches were extracted with ethyl acetate several times. The combined ethyl acetate layers were dried with sodium sulfate, treated with activated carbon, filtered over diatomaceous earth, and washed with ethyl acetate. The filtrate was evaporated at 40-70 mm Hg with a bath temperature of 23° C.-40° C. to give bio-based acrylic acid as a pale yellow liquid (81.4% yield). The bio-based acrylic acid was then fractionally distilled using a 12 inch 14/20 Vigreux column. The product was collected with head temperature of 59-62° C., stabilized with 4-methoxy phenol, and placed in a 3-5° C. fridge overnight. The solution was removed from the fridge and thawed slightly. The resulting liquid was decanted off and the solids were combined. The crystallization was repeated several times. The four batches were combined to give glacial acrylic acid (218 g, 32.6% yield on purification). The glacial acrylic acid composition consisted of 99.1 wt % acrylic acid, 0.1 wt % water, 0.7 wt % propanoic acid, and 0.1 wt % lactic acid.

Example 5

The cross-linker methylene bis-acrylamide (MBAA; 0.963 g, 0.006 mol) was dissolved in bio-based acrylic acid from Example 4 (150 g, 2.08 mol) by stirring in a holding beaker. The solution was then added dropwise via a pipette while stirring to 124.9 g of 50 wt % solution of NaOH (1.56 mol) in a 1 L reactor equipped with magnetic stirrer. The reactor was placed in an ice bath to remove the heat released by the neutralization. A small amount of water (10 g) was used to rinse the pipette and original bio-based acrylic acid/MBAA holding beaker. Once the temperature of the neutralized acrylic acid became about 20° C., the reactor was removed from the ice bath. Water was added to the reaction mixture to make the whole weight of the mixture equal to 474 g. The reactor was then closed and insulated (Baysilone paste for insulation of the glass surfaces of vessel and lid, in addition to Teflon tape on the outside where the lid met the vessel). The reaction mixture was purged with argon for at least 20 min. The reactor was equipped with a syringe needle to allow for pressure equilibration. The reactor was then placed on a stir plate. 0.15 g of the initiator V50 (2,2'-azobis(2-methylpropionamidine)dihydrochloride; Wako Pure Chemical Industries, Ltd; Osaka, Japan) was injected in the mixture while stirring and was allowed to homogenize for another 10 min. Two UV lamps equipped with side mirrors were placed on both sides of the reactor in a way to surround it as much as possible. When the light was turned on, the temperature vs. time started being recorded. The reaction temperature started increasing after certain time and reached typically 40° C. to 70° C., after which it starts slowly decreasing. The gellation was observed by the decreasing rotation speed of the stir bar, which then came to a complete stop. After the temperature started dropping steadily below the maximum point (about 30 min after the temperature started increasing above room temperature), the reactor was removed and placed in a circulation oven preset at 60° C. and stayed there overnight (at least 18 hours). On the next day, the reactor was removed from the oven and allowed to cool for one hour. The gel was carefully removed from the reactor and wet-ground through a steel mesh onto several Teflon-ized metal trays that were then placed in an oven at 80° C. and 10 mbar vacuum over 3 days. The dried superabsorbent polymer was then milled in a regular commercial mill (Retsch GmbH; Haan, Germany) and sieved through a set of meshes to obtain the 150 μm-850 μm particle size distribution cut. The so obtained superabsorbent polymer powder was tested for cylinder retention capacity (CRC), extractables, and absorption against pressure (AAP). The results were the same as those obtained from the testing of petroleum-based superabsorbent polymer, prepared under the same conditions as the bio-based superabsorbent polymer, to within experimental error.

Example 6

The superabsorbent polymer powder of Example 5 was tested for cylinder retention capacity (CRC), extractables, and absorption against pressure (AAP) using the methods described the "Test and Calculation Procedures" section below. The results are shown in Table 1 below, along with results from the same tests on petroleum-based SAP prepared under the same conditions as in Example 5.

TABLE 1

|  | SAP Property | |
| --- | --- | --- |
|  | Bio-based SAP | Petroleum-based SAP |
| Cylinder retention capacity (CRC), [g/g] | 43.3 | 40.2 |
| Extractables, [%] | 7.3 | 7.7 |
| Absorption against pressure (AAP), [g/g] | 34.4 | 33.1 |

The results showed that bio-based SAP and petroleum-based SAP had the same properties, to within experimental error.

Example 7

The bio-based content of the superabsorbent polymer composition of Example 4 is measured in accordance with ASTM D6866 Method B, as described in the Test and Calculation Procedures section below, and is greater than about 90%.

VIII Test and Calculation Procedures

Extractables: the extractable fractions of the water-absorbing superabsorbent polymer particles are measured in accordance with INDA test method WSP 270.2, incorporated herein by reference.

Cylinder retention capacity (CRC): it is measured in accordance with INDA test method WSP 241.2, incorporated herein by reference.

Absorption against pressure (AAP): it is measured in accordance with INDA test method WSP 242.2, incorporated herein by reference.

Residual monomer: it is measured in accordance with INDA test method WSP 210.2, incorporated herein by reference.

The above tests and measurements should be carried out, unless otherwise stated, at an ambient temperature of 23±2° C. and relative humidity of 50±10%.

Bio-based content: the bio-based content of a material is measured using the ASTM D6866 method, which allows the determination of the bio-based content of materials using radiocarbon analysis by accelerator mass spectrometry, liquid scintillation counting, and isotope mass spectrometry. When nitrogen in the atmosphere is struck by an ultraviolet light produced neutron, it loses a proton and forms carbon that has a molecular weight of 14, which is radioactive. This $^{14}C$ is immediately oxidized into carbon dioxide, which represents a small, but measurable fraction of atmospheric carbon. Atmospheric carbon dioxide is cycled by green plants to make organic molecules during the process known as photosynthesis. The cycle is completed when the green plants or other forms of life metabolize the organic molecules producing carbon dioxide, which causes the release of carbon dioxide back to the atmosphere. Virtually all forms of life on Earth depend on this green plant production of organic molecules to produce the chemical energy that facilitates growth and reproduction. Therefore, the $^{14}C$ that exists in the atmosphere becomes part of all life forms and their biological products. These renewably based organic molecules that biodegrade to carbon dioxide do not contribute to global warming because no net increase of carbon is emitted to the atmosphere. In contrast, fossil fuel-based carbon does not have the signature radiocarbon ratio of atmospheric carbon dioxide. See WO 2009/155086, incorporated herein by reference.

The application of ASTM D6866 to derive a "bio-based content" is built on the same concepts as radiocarbon dating, but without use of the age equations. The analysis is performed by deriving a ratio of the amount of radiocarbon ($^{14}C$) in an unknown sample to that of a modern reference standard. The ratio is reported as a percentage with the units "pMC" (percent modern carbon). If the material being analyzed is a mixture of present day radiocarbon and fossil carbon (containing no radiocarbon), then the pMC value obtained correlates directly to the amount of biomass material present in the sample. The modern reference standard used in radiocarbon dating is a NIST (National Institute of Standards and Technology) standard with a known radiocarbon content equivalent approximately to the year AD 1950. The year AD 1950 was chosen because it represented a time prior to thermo-nuclear weapons testing, which introduced large amounts of excess radiocarbon into the atmosphere with each explosion (termed "bomb carbon").

The AD 1950 reference represents 100 pMC. "Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. The distribution of bomb carbon has gradually decreased over time, with today's value being near 107.5 pMC. As a result, a fresh biomass material, such as corn, could result in a radiocarbon signature near 107.5 pMC.

Petroleum-based carbon does not have the signature radiocarbon ratio of atmospheric carbon dioxide. Research has noted that fossil fuels and petrochemicals have less than about 1 pMC, and typically less than about 0.1 pMC, for example, less than about 0.03 pMC. However, compounds derived entirely from renewable resources have at least about 95 percent modern carbon (pMC), they may have at least about 99 pMC, including about 100 pMC.

Combining fossil carbon with present day carbon into a material will result in a dilution of the present day pMC content. By presuming that 107.5 pMC represents present day biomass materials and 0 pMC represents petroleum derivatives, the measured pMC value for that material will reflect the proportions of the two component types. A material derived 100% from present day soybeans would give a radiocarbon signature near 107.5 pMC. If that material was diluted with 50% petroleum derivatives, it would give a radiocarbon signature near 54 pMC.

A bio-based content result is derived by assigning 100% equal to 107.5 pMC and 0% equal to 0 pMC. In this regard, a sample measuring 99 pMC will give an equivalent bio-based content result of 93%.

Assessment of the materials described herein was done in accordance with ASTM D6866, particularly with Method B. The mean values encompass an absolute range of 6% (plus and minus 3% on either side of the bio-based content value) to account for variations in end-component radiocarbon signatures. It is presumed that all materials are present day or fossil in origin and that the desired result is the amount of bio-component "present" in the material, not the amount of bio-material "used" in the manufacturing process.

Other techniques for assessing the bio-based content of materials are described in U.S. Pat. Nos. 3,885,155, 4,427,884, 4,973,841, 5,438,194, and 5,661,299, and WO 2009/155086, each incorporated herein by reference.

For example, acrylic acid contains three carbon atoms in its structural unit. If acrylic acid is derived from a renewable resource, then it theoretically has a bio-based content of 100%, because all of the carbon atoms are derived from a renewable resource.

The foregoing description is given for clearness of understanding only, and no unnecessary limitations should be understood therefrom, as modifications within the scope of the invention may be apparent to those having ordinary skill in the art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A superabsorbent polymer composition produced from an acrylic composition, wherein said acrylic composition comprises an acrylic acid composition, wherein said acrylic acid composition consists of acrylic acid, acrylic acid derivatives, or mixtures thereof, wherein said acrylic acid composition comprises at least about 98 wt % acrylic acid, acrylic acid derivatives, or mixtures thereof, and wherein a portion of the remaining impurities in said acrylic acid composition is lactic acid, lactic acid derivatives, or mixtures thereof; and further, wherein said superabsorbent polymer is produced by the steps comprising:
   a. Preparing a pre-polymerization solution comprising glacial acrylic acid, methylene bis-acrylamide, and water;
   b. Mixing sodium hydroxide into said pre-polymerization solution to form a partially neutralized acrylic acid solution;
   c. Combining 2,2'-azobis(2-methylpropionamidine)dihydrochloride with said partially neutralized acrylic acid solution to produce a polymerization mixture;
   d. Polymerizing said polymerization mixture using UV light to produce a gel; and
   e. Drying said gel to produce the superabsorbent polymer composition.

2. The composition of claim 1, wherein the amount of said acrylic acid composition in said pre-polymerization solution is from about 5 wt % to about 95 wt %.

3. The superabsorbent polymer composition of claim 1 having a bio-based content greater than about 3%.

4. The superabsorbent polymer composition of claim 1 having a bio-based content greater than about 30%.

5. The superabsorbent polymer composition of claim 1 having a bio-based content greater than about 90%.

6. The superabsorbent polymer composition of claim 1, wherein said acrylic acid composition has a bio-based content greater than about 3%.

7. The superabsorbent polymer composition of claim 1, wherein said acrylic acid composition has a bio-based content greater than about 30%.

8. The superabsorbent polymer composition of claim 1, wherein said acrylic acid composition has a bio-based content greater than about 90%.

9. The superabsorbent polymer composition of claim 1, wherein said polymer composition has a cylinder retention capacity (CRC) between about 20 g/g and about 45 g/g.

10. The superabsorbent polymer composition of claim 1, wherein said polymer composition has a cylinder retention capacity (CRC) between about 25 g/g and about 40 g/g.

11. The superabsorbent polymer composition of claim 1, wherein said polymer composition has a cylinder retention capacity (CRC) between about 30 g/g and about 35 g/g.

12. The superabsorbent polymer composition of claim 1, wherein said polymer composition has an extractables value from about 0 wt % to about 20 wt %.

13. The superabsorbent polymer composition of claim 1, wherein said polymer composition has an extractables value from about 3 wt % to about 15 wt %.

14. The superabsorbent polymer composition of claim 1, wherein said polymer composition has an extractables value from about 5 wt % to about 10 wt %.

15. The superabsorbent polymer composition of claim 1, wherein said polymer composition has absorption against pressure (AAP) between about 15 g/g and about 40 g/g.

16. The superabsorbent polymer composition of claim 1, wherein said polymer composition has absorption against pressure (AAP) between about 20 g/g and about 35 g/g.

17. The superabsorbent polymer composition of claim 1, wherein said polymer composition has absorption against pressure (AAP) between about 25 g/g and about 30 g/g.

18. The superabsorbent polymer composition of claim 1, wherein the amount of residual monomers in said polymer is about 500 ppm or less.

19. An absorbent article selected from adult incontinence garments, infant diapers, and feminine hygiene articles, comprising the superabsorbent polymer composition of claim 1.

20. An absorbent article having opposing longitudinal edges, the absorbent article comprising:
  a. a top sheet,
  b. a back sheet joined with the top sheet; and
  c. an absorbent core disposed between the top sheet and the back sheet, and wherein, the absorbent core comprises a superabsorbent polymer composition according to claim 1.

* * * * *